United States Patent [19]

Lowe, III

[11] Patent Number: 5,618,811

[45] Date of Patent: Apr. 8, 1997

[54] TETRAHYDRO-1H-BENZAZEPINONES AND HEXAHYDROAZEPINONES AS SELECTIVE CHOLECYSTOKININ-B RECEPTOR ANTAGONISTS

[75] Inventor: John A. Lowe, III, Stonington, Conn.

[73] Assignee: Pfizer Inc., New York, N.Y.

[21] Appl. No.: 586,685

[22] PCT Filed: May 19, 1994

[86] PCT No.: PCT/IB94/00111

§ 371 Date: Jan. 18, 1996

§ 102(e) Date: Jan. 18, 1996

[87] PCT Pub. No.: WO95/03281

PCT Pub. Date: Feb. 2, 1995

Related U.S. Application Data

[63] Continuation of Ser. No. 97,640, Jul. 26, 1993, abandoned.

[51] Int. Cl.$^6$ .......................... A61K 31/55; C07D 223/12
[52] U.S. Cl. ........................... 514/218; 514/221; 540/523; 540/524; 540/527
[58] Field of Search ..................... 540/523, 524, 540/527; 514/218, 221

[56] References Cited

FOREIGN PATENT DOCUMENTS

| 487207 | 5/1992 | European Pat. Off. ........ A61K 31/55 |
| WO/15059 | 8/1993 | WIPO ............................ A61K 31/55 |

*Primary Examiner*—Robert T. Bond
*Attorney, Agent, or Firm*—P. C. Richardson; P. H. Ginsburg; B. C. Zielinski

[57] ABSTRACT

This invention relates to compounds of formula (I) wherein $R^1$, $R^2$, $R^3$, $R^4$ and X are as defined in the application. These compounds are CCK-B receptor antagonists and are useful in the treatment and prevention of central nervous system and gastrointestinal disorders.

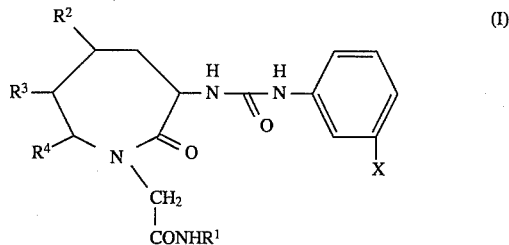

13 Claims, No Drawings

TETRAHYDRO-1H-BENZAZEPINONES AND HEXAHYDROAZEPINONES AS SELECTIVE CHOLECYSTOKININ-B RECEPTOR ANTAGONISTS

This application is a continuation of Ser. No. 08/097,640, filed 26 Jul. 1993, now abandoned and PCT/IB94/00111 having a PCT filing date of 19 May 1994 and now WO 95/03281, published 2 Feb. 1995.

The present invention relates to novel azepinones containing acid surrogates, pharmaceutical compositions comprising such compounds and the use of such compounds in the treatment and prevention of central nervous system and gastrointestinal disorders. The pharmaceutically active compounds of this invention are selective CCK-B receptor antagonists.

Cholecystokinin (CCK) is a 33-amino acid peptide originally discovered and characterized in 1971. (See Mutt et al., *Biochem. J.*, 125, 57 (1971)). It carries out its biological responses by binding to its two receptor types: CCK-A and CCK-B. The CCK-A receptor is located primarily in the gallbladder and pancreas, and mediates CCK-induced enzyme secretion and gallbladder contraction during a meal. The CCK-B receptor is located in the stomach, where it is involved in acid secretion, and in the brain, where it mediates pain and anxiety responses.

A number of potent and selective non-peptide antagonists for these two receptors are known (See M. G. Bock, *Drugs of the Future*, 16 (7), 631–640 (1991) and R. M. Freidinger, *Med. Res. Rev.*, 9, 271–290 (1989)). Merck's L-364,718 (devazepide) is a selective CCK-A antagonist. (See O'Neill et al., *Brain Res.*, 534, 287–290 (1990)). This compound, however, has proven not to be clinically useful. Merck's benzodiazepine L-365,260 is a selective CCK-B antagonist that was found to have an analgesic effect on squirrel monkeys. (See O'Neill et al., *Brain Res.*, 534, 287–290 (1990)). Parke-Davis' CI-988 is a selective CCK-B antagonist that was found to reverse the pentagastrin-induced anxiogenic response in rats. (See Singh et al., *Proc. Nat'l. Acad. Sci., U.S.*, 88, 1130–33 (1991)).

Other selective CCK-B antagonists are referred to in U.S. patent application 07/825,677, which was filed on Jan. 27, 1992 and PCT patent application PCT/US 92/10720, which was filed in the U.S. Receiving Office on Dec. 16, 1992.

The present invention relates to compounds of the formula

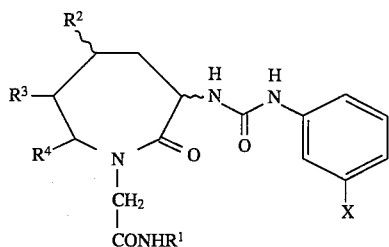

I wherein $R^1$ is $(C_1-C_{10})$alkyl;

$R^2$ is phenyl or $(C_1-C_{10})$alkyl, each of which may be substituted by $Y^1$;

$R^3$ and $R^4$ are independently selected from the group consisting of hydrogen, $(C_1-C_{10})$alkyl and phenyl, or may be taken together with the two carbons to which they are attached to form a phenyl which may be substituted by $Y^2$;

X is tetrazolyl or

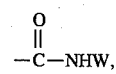

wherein W is selected from

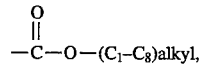

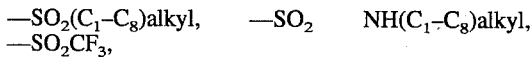

—$SO_2CF_3$,

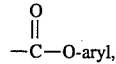

—$SO_2$(phenyl), —$SO_2$(benzyl), —$SO_2$ NH(phenyl), —$SO_2$ NH(heteroaryl) and —$SO_2$(heteroaryl), wherein said heteroaryl is a 5 to 7 membered saturated or unsaturated hydrocarbon ring containing one to four heteroatoms selected from oxygen, nitrogen and sulfur and wherein the phenyl and heteroaryl moieties of W may optionally be substituted with one or two substituents independently selected from $(C_1-C_6)$alkyl optionally substituted with from one to three fluorine atoms, phenyl, halo, $(C_1-C_6)$alkoxy optionally substituted with from one to three fluorine atoms,

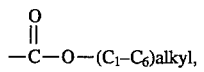

—$SO_2$, —$SO_2$ $NH_2$, —$SO_2$ $NH(C_1-C_6)$alkyl,

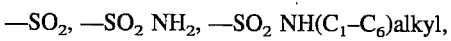

cyano and —$S(C_1-C_6)$alkyl; and $Y^1$ and $Y^2$ are independently selected from the group consisting of hydrogen, thienyl, pyridyl, furyl, and pyrimidyl, halo, $(C_1-C_6)$ alkyl optionally substituted with from one to three fluorine atoms, $(C_1-C_6)$ alkoxy optionally substituted with from one to three fluorine atoms, nitro, cyano, amino, —$NH(C_1-C_6)$alkyl, —$N[(C_1-C_8)$alkyl$]_2$, —$S$—$(C_1-C_8)$alkyl, —$SO$—$(C_1-C_8)$alkyl, —$SO_2$—$(C_1-C_8)$alkyl,

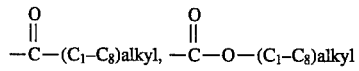

and phenyl, wherein said phenyl may optionally be substituted with one or two substituents independently selected from halo, $(C_1-C_6)$alkyl, $(C_1-C_6)$alkoxy, nitro, cyano, amino and trifluoromethyl;
or a pharmaceutically acceptable salt thereof.

Preferred compounds of formula I include those wherein $R^2$ is phenyl, isopropyl or cyclohexyl.

Preferred compounds of formula I include those wherein $R^3$ is hydrogen and $R^4$ is phenyl.

Preferred compounds of formula I include those wherein $R^3$ and $R^4$ are taken together with the two carbons to which they are attached to form a phenyl group.

Preferred compounds of formula I include those wherein $R^2$ is phenyl, $R^3$ is hydrogen and $R^4$ is phenyl.

Preferred compounds of formula I include those wherein $R^2$ is phenyl and $R^3$ and $R^4$ are taken together with the two carbons to which they are attached to form a phenyl group.

Preferred compounds of formula I include those wherein $R^2$ is isopropyl and $R^3$ and $R^4$ are taken together with the two carbons to which they are attached to form a phenyl group.

Preferred compounds of formula I include those wherein $R^2$ is cyclohexyl and $R^3$ and $R^4$ are taken together with the two carbons to which they are attached to form a phenyl group.

Preferred compounds of formula I include those wherein X is $CONHSO_2(C_1-C_8)$alkyl or tetrazolyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)] salts.

The term "alkyl", as used herein, unless otherwise indicated, includes saturated monovalent hydrocarbon radicals having straight, branched or cyclic moieties or combinations thereof.

The term "halo", as used herein, unless otherwise indicated, includes chloro, fluoro, bromo and iodo.

Preferred compounds of the present invention include the following:

N-(1-t-butyl)-2-[3-((3-N-(methanesulfonamido)carboxamido)phenyl)ureido-2-oxo-5-(phenyl)-8-methyl-2, 3, 4, 5-tetrahydro-1H-(1)benzazepin-1-yl]ethanoic acid amide; and N-(1-t-butyl)-2-[3-((3-N-(phenylsulfonamido)carboxamido)phenyl)ureido)-2-oxo-5-(phenyl)-8-methyl-2, 3, 4, 5-tetrahydro-1H-(1)benzazepin-1-yl]ethanoic acid amide.

Other compounds of this invention include the following:

N-(1-t-butyl)-2-[3-((3-N-(trifluoromethanesulfonamido)carboxamido)phenyl)ureido-2-oxo-5-(phenyl)-8-methyl-2,3,4,5-tetrahydro-1H-(1)benzazepin-1-yl]ethanoic acid amide;

N-(1-t-butyl)-2-[3-((3-N-(p-tolylsulfonamido)carboxamido)phenyl)ureido)-2-oxo-5-(phenyl)-8-methyl-2,3,4,5-tetrahydro-1H-(1)benzazepin-1-yl]ethanoic acid amide;

N-(1-t-butyl)-2-[3-((3-N-(isopropylsulfonamido)carboxamido)phenyl)ureido)-2-oxo-5-(phenyl)-8-methyl-1,2,3,4,5-tetrahydro-1H-(1)benzazepin-1-yl]ethanoic acid amide;

N-(1-t-butyl)-2-[3-((3-N-(benzylsulfonamido)carboxamido)phenyl)ureido)-2-oxo-5-(phenyl)-8-methyl-2,3,4,5-tetrahydro-1H-(1)benzazepin-1-yl]ethanoic acid amide;

N-(1-t-butyl)-2-[3-((3-N-(butylsulfonamido)carboxamido)phenyl)ureido)-2-oxo-5-(phenyl)-8-methyl-2,3,4,5-tetrahydro-1H-(1)benzazepin-1-yl]ethanoic acid amide;

N-(1-t-butyl)-2-[3-((3-N-(propylsulfonamido)carboxamido)phenyl)ureido)-2-oxo-5-(phenyl)-8-methyl-2,3,4,5-tetrahydro-1H-(1)benzazepin-1-yl]ethanoic acid amide;

N-(1-t-butyl)-2-[3-((3-N-(isobutylsulfonamido)carboxamido)phenyl)ureido)-2-oxo-5-(phenyl)-8-methyl-2,3,4,5-tetrahydro-1H-(1)benzazepin-1-yl]ethanoic acid amide;

N-(1-t-butyl)-2-[3-((3-N-(tert-butylsulfonamido)carboxamido)phenyl)ureido)-2-oxo-5-(phenyl)-8-methyl-2,3,4,5-tetrahydro-1H-(1)benzazepin-1-yl]ethanoic acid amide;

N-(1-t-butyl)-2-[3-((5-tetrazolyl)phenyl)ureido)-2-oxo-5-(phenyl)-8-methyl-2,3,4,5-tetrahydro-1H-(1)benzazepin-1yl]ethanoic acid amide;

N-(1-t-butyl)-2-[3-((3-N-(benzoyl)carboxamido)phenyl)ureido)-2-oxo-5-(phenyl)-8-methyl-2,3,4,5-tetrahydro-1H-(1)benzazepin-1-yl]ethanoic acid amide;

N-(1-t-butyl)-2-[3-((3-N-(acetyl)carboxamido)phenyl)ureido)-2-oxo-5-(phenyl)-8-methyl-2,3,4,5-tetrahydro-1H-(1)benzazepin-1-yl]ethanoic acid amide; and N-(1-t-butyl)-2-[3-((3-N-(phenylcarboxamido)carboxamido)phenyl)ureido)-2-oxo-5-(phenyl)-8-methyl-2,3,4,5-tetrahydro-1H-(1)benzazepin-1-yl]ethanoic acid amide.

The present invention also relates to a pharmaceutical composition for treating or preventing a condition selected from the group consisting of pain, gastrointestinal disorders such as ulcer and colitis, and central nervous system disorders such as anxiety and panic disorder in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of pain, gastrointestinal disorders such as ulcer and colitis, and central nervous system disorders such as anxiety and panic disorder in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of cholecystokinin in a mammal, including a human, comprising a cholecystokinin antagonizing amount of a compound of the formula I, or a pharmaceutically acceptable salt thereof, and a pharmaceutically acceptable carrier.

The present invention also relates to a method of antagonizing the effects of cholecystokinin in a mammal, including a human, comprising administering to said mammal a cholecystokinin antagonizing amount of a compound of the formula I, or a pharmaceutically acceptable salt thereof.

The present invention also relates to a pharmaceutical composition for treating or preventing a cholecystokinin mediated disorder in a mammal, including a human, comprising a cholecystokinin antagonizing amount of a compound of the formula I, or a pharmaceutically acceptable salt thereof, and a pharmaceutically acceptable carrier.

The present invention also relates to a method of treating or preventing a cholecystokinin medicated disorder in a mammal, including a human, comprising administering to said mammal a cholecystokinin antagonizing amount of a compound of the formula I, or a pharmaceutically acceptable salt thereof.

The present invention also relates to a pharmaceutical composition for treating or preventing a condition selected from the group consisting of pain, gastrointestinal disorders such as ulcer and colitis, and central nervous system disorders such as anxiety and panic disorder in a mammal, including a human, comprising an amount of a compound of the formula I, or a pharmaceutically acceptable salt thereof, effective in antagonizing the effect of cholecystokinin at its receptor site, and a pharmaceutically acceptable carrier.

The present invention also relates to a method of treating or preventing a condition selected from the group consisting of pain, gastrointestinal disorders such as ulcer and colitis, and central nervous system disorders such as anxiety and panic disorder in a mammal, including a human, comprising administering to said mammal an amount of a compound of the formula I, or a pharmaceutically acceptable salt thereof, effective in antagonizing the effect of cholecystokinin at its receptor site.

The compounds of the formula I have chiral centers and therefore exist in different enantiomeric and diastereomic forms. This invention relates to all optical isomers and all stereoisomers of compounds of the formula I, and mixtures thereof.

Formula I above include compounds identical to those depicted but for the fact that one or more hydrogen or carbon atoms are replaced by isotopes thereof. Such compounds are useful as research and diagnostic tools in metabolism pharmacokinetic studies and in binding assays.

The compounds of the formula I may be prepared as described in the following reaction schemes and discussion. Unless otherwise indicated, $R^1$, $R^2$, $R^3$, $R^4$ and X in the reaction scheme and discussion that follow are defined as above.

SCHEME

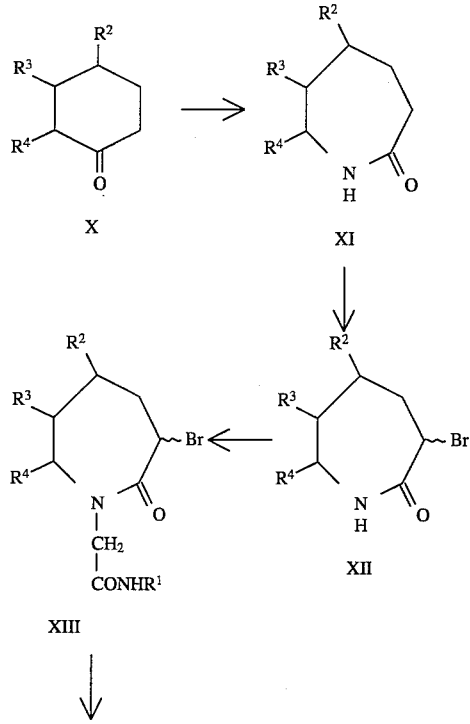

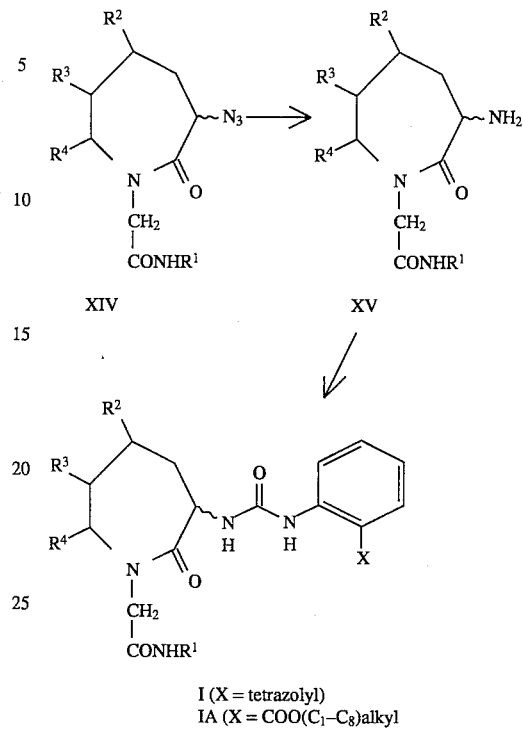

I (X = tetrazolyl)
IA (X = COO($C_1$–$C_8$)alkyl)

The preparation of compounds of the formula I wherein X is tetrazolyl and related compounds wherein X is replaced by

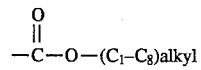

—C—O—($C_1$–$C_8$)alkyl (hereinafter referred to as compounds of the formula IA) is illustrated in the above reaction scheme. As discussed below, compounds of the formula I wherein X is other than tetrazolyl can be formed from the corresponding esters of the formula IA.

Referring to the Scheme, a compound of the formula X is converted into the corresponding compound of formula XII by the following two step procedure. First, the compound of formula X is converted into an oxime. Then, rearrangement of the oxime to form the lactam having formula XI is accomplished by reacting the oxime with polyphosphoric acid. This reaction may be carried out at temperatures ranging from about room temperature to about 200° C. Preferably, the reaction mixture is heated to about 160° C.

The resulting compound of formula XI is then brominated to form a compound of the formula XII by first reacting it with phosphorous pentachloride and pyridine, and then adding bromine. The reaction with phosphorus pentachloride and pyridine is conducted as described above for the first step in the bromination of compounds of the formula V. The reaction with bromine, which results in monobromination, is carried out at a temperature from about −78° C. about 0° C., preferably at about −40° C.

Alkylation of the compound of formula XII yields the corresponding compound of formula XIII. The alkylation is carried out by reacting the compound of formula XII with a compound of the formula X'CH$_2$CONHR$^1$, wherein X' is iodine, in tetrahydrofuran/dimethylsulfoxide (THF/DMSO) in the presence of lithium dialkylamide. It is preferable to add the DMSO cosolvent after adding the lithium dialkylamide. The reaction temperature may range from about −78° C. to about 0° C. during addition of the base, and is preferably about −78° C. The reaction is slowly warmed to a temperature from about −20° C. to about 50° C. when the DMSO is added. Preferably, the reaction is warmed to about room temperature during addition of DMSO.

The compound of formula XIII formed in the above step is then reacted with an alkali metal azide to produce a compound of the formula XIV. The preferred reactant is sodium azide. Generally, this reaction is carried out in a reaction inert solvent such as dimethylformamide (DMF) or dimethylsulfoxide (DMSO), preferably DMF, at a temperature from about 60° C. to about 100° C., preferably about 80° C.

Reduction of the azide of formula XIV yields the corresponding amine of formula XV. The reduction is typically accomplished using hydrogen gas at a pressure of from about 1 to about 3 atmospheres in the presence of palladium on carbon (Pd/C). Suitable reaction inert solvents include halogenated hydrocarbons and (C$_1$–C$_6$) alkanols. Ethanol is the preferred solvent. The reaction temperature may range from about 15° C. to about 70° C., with about room temperature being preferred.

Alternatively, the reduction may be accomplished using a trialkyl or triaryl phosphine. Examples of appropriate reactants are triphenylphosphine and tributylphosphine. This reaction is generally conducted in a reaction inert solvent such as THF or another ethereal water miscible solvent in the presence of water, at a temperature from about room temperature to about 100° C. Preferably, it is conducted in THF at about room temperature.

The compound of formula XV so formed is then converted into the corresponding compound having formula I by reacting it with an isocyanate of the formula C$_6$H$_4$XNCO, wherein X is tetrazolyl or

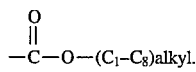

Appropriate reaction inert solvents for this reaction include hydrocarbons such as hexane, benzene and toluene, halogenated hydrocarbons such as methylene chloride and 1,2-dichloroethane, ethereal solvents such as ethyl ether, THF and glyme, and pyridine. The preferred solvent is 1,2-dichloroethane or methylene chloride. Tertiary organic amines may be useful as catalysts. The reaction temperature may range from about 0° C. to about 150° C. The reflux temperature is preferred.

The isocyanate of the formula C$_6$H$_4$Z$^1$Z$^2$NCO used in the foregoing reaction can be formed by procedures well known to those skilled in the art. One such method involves mixing a benzoic acid derivative with diphenylphosphorylazide, or an analagous reagent, in the presence of an organic base such as a trialkylamine, preferably triethylamine or diisopropylethylamine. This reaction is usually conducted in an ethereal, hydrocarbon or chlorinated hydrocarbon solvent, preferably tetrahydrofuran or benzene, at a temperature from about room temperature to about 100° C., preferably at the reflux temperature of the solvent, for a period from about 20 minutes to about 24 hours, preferably about 1 hour.

Compounds of the formula I wherein X is other than tetrazolyl or carboalkoxy may be prepared from the corresponding esters wherein X is replaced by CO$_2$R$^5$, wherein R$^5$ is an alkyl, aryl or aralkyl group that will permit hydrolysis of the ester (e.g., methyl, t-butyl or benzyl). Such esters may be prepared by the method described above and depicted in the reaction scheme by replacing the reactant C$_6$H$_4$XNCO used in the conversion of compounds of the formula XV into compounds of the formula I with, respectively, C$_6$H$_4$CO$_2$R$^5$NCO, wherein R$^5$ is defined as above.

The corresponding acids may be prepared by hydrolysis of the esters. Such hydrolysis is usually accomplished by treating the ester with an alkali metal hydroxide, preferably lithium hydroxide, in a solvent consisting of water, an alcohol, and/or an ethereal solvent such as tetrahydrofuran or dioxane. Preferably, the ester is dissolved in tetrahydrofuran, after which lithium hydroxide dissolved in water is added, followed by sufficient methanol to produce a solution. The reaction is stirred at a temperature from about 0° C. to reflux, with room temperature being preferred, for a period of from about 1 to 48 hours, preferably about 18 hours.

The acid may be converted into the corresponding acyl urea or acyl sulfonamide of formula I wherein X is —CONHSO$_2$(C$_1$–C$_8$)alkyl, —CONHSO$_2$(phenyl), —CONHCO$_2$R$^2$ or —CONHCONHR$^2$ by treating it with the appropriate compound of the formula R$^2$SO$_2$NH$_2$, R$^2$CO$_2$NH$_2$ or R$^2$NHCONH$_2$, wherein R$^2$ is (C$_1$–C$_8$)alkyl, phenyl or heteroaryl, in the presence of a dehydrating reagent and an organic base. The dehydrating agent is usually a carbodiimide. N-ethyl,N-(dimethylaminopropyl) carbodiimide is preferred. The organic base is usually a tertiary amine such as triethylamine or 4-N,N-dimethylaminopyridine, with N-ethyl, N-(dimethylaminopropyl)carbodiimide being preferred. Typically, the reaction is conducted in an ethereal, halogenated hydrocarbon, or polar aprotic solvent, with dimethylformamide being preferred. The reaction is carried out at a temperature from 0° C. to 100° C., with room temperature being preferred, for a period of from 1 hour to 48 hours, with 14 hours being preferred. An additive, such as N-hydroxysuccinimide or N-hydroxybenzotriazole, may be used if desired.

The starting materials used in the above procedures are either commercially available, known in the art or readily obtainable form known compounds by methods that will be apparent to those skilled in the art.

The preparation of other compounds of the formula I not specifically described in the foregoing experimental section can be accomplished using combinations of the reactions described above that will be apparent to those skilled in the art.

In each of the reactions discussed or illustrated in the Scheme above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The compounds of the invention contain chiral centers. It is understood that the invention includes the racemic mixtures and the individual enantiomers of such compounds.

The compounds of formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of this invention (the compounds of formula I and their pharmaceutically acceptable salts) are useful as selective CCK-B receptor antagonists, i.e., they possess the ability to antagonize the effects of CCK at its B receptor site in mammals, and therefore they are able to function as therapeutic agents in the treatment of the aforementioned disorders and diseases in an afflicted mammal.

The compounds of this invention can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as CCK-B antagonists may be determined by an assay that measures their ability to inhibit the binding of 125-I-BH-CCK-8 to the CCK-B receptor in a guinea pig cortical membrane preparation. This procedure is carried out as follows. The cortex is dissected from one male Hartley Guinea pig and homogenized (15 strokes) with a teflon homogenizer in 20 volumes (w./v.) of the assay buffer, which consists of 50 mM Tris (i.e., trimethamine, which is 2-amino-2-hydroxymethyl-1,3-propanediol) hydrochloric acid having pH 7.4 and 5 mM of manganese chloride at 4° C. The homogenate is centrifuged at 4° C. for 30 minutes at 100,000× G. The pellet is resuspended in the same buffer and spun as described above. The final pellet is diluted to a concentration of 20 mg/ml with the assay buffer for use in the binding assay. The tissue is kept on ice at all times.

An incubation mixture is prepared, which consists of 50 uL of the tissue preparation, prepared as described above, 100 uL 125-I-BH-CCK-8 (to give a concentration of 50 pM in the final assay), 20 uL of a blank or the compound being tested, and 30 uL of Tris with 4% DMSO. All drugs and dilutions are made using 4% DMSO in the assay buffer yielding a final assay DMSO concentration of 1%.

The reaction is initiated with the addition of tissue to a 96-well plate containing 125-I-BH-CCK-8 and the appropriate blank or compound being tested. Non-specific binding is estimated using 1 uM sulphated CCK-8. The reaction is terminated by spinning the plates in a H1000B rotor fitted on a Sorvall RT6000 refrigerated centrifuge at 4° C. . The supernatant is discarded, and the pellets washed with 200 uL of assay buffer, and the plate is spun as above. The supernatant is decanted again, and the pellet is harvested onto Betaplate filters (which have been soaked in 0.2% polyethyleneimine for a minimum of 2 hours) using a Skatron cell harvester at setting 222 using Tris hydrochloric acid pH 7.4 as the wash buffer. The filtermats are counted on a Betaplate counter for 45 seconds per sample.

Data are expressed as $IC_{50}$ values (the concentration which inhibits 50% of the specific binding of 125-I-BH-CCK8). The data is analyzed using non-linear regression analysis.

The present invention is illustrated by the following examples. It will be, understood, however, that the invention is not limited to the specific details of these examples.

PREPARATION A

N-tert-Butyl-2-(3-amino-2-oxo-5-phenyl-2,3,4,5-tetrahydro-1H-(1)benzazepin-1-yl) ethanoic acid amide A. 4-(4-Methylphenyl)butyric acid To a 2 liter round-bottomed flask equipped with condenser and drying tube were added 68 grams (0.68 mol) succinic anhydride, 478 ml dry toluene, and 140 grams (1.05 mol) aluminum chloride in three portions (allowing the brisk hydrochloric acid evolution to subside after each portion). The reaction was heated until evolution of hydrogen chloride gas ceased, and then was cooled and quenched by dropwise addition of 200 mL water. Swirling was continued as 100 mL concentrated hydrochloric acid was added. The resulting solid was filtered, washed with 1N hydrochloric acid, water, and hexane three times, and then dried to a white solid (M.P. 122°–126° C.) which still contained aluminum salts and water, but was suitable for the following step.

To a 2L round-bottomed flask equipped with condenser were added 240 grams mossy zinc, 24 grams mercuric chloride, 400 mL water, and 11 mL concentrated hydrochloric acid. After swirling for 5 minutes, the aqueous layer was decanted, and the solid washed with a little water. To the residue were added 150 mL water, 350 mL concentrated hydrochloric acid (causing an exotherm and gas evolution), 200 mL toluene, and the above solid. The mixture was heated to reflux, and 50 mL concentrated hydrochloric acid was added after each of 5, 7, 9, and 22 hours. After 25 hours at reflux, the reaction was cooled, the layers separated, and the aqueous layer washed with ether. The combined organic layers were washed with water and brine, dried over sodium sulfate, and evaporated to give a solid, 103 grams (85% for 2 steps).

$^1$H NMR ($\delta$, CDCl$_3$): 2.00 (m, 2H), 2.37 (s, 3H), 2.42 (t, J=7, 2H), 2.69 (t, J=7, 2H), 7.14 (m, 4H).

B. 1-Acetoxy-7-methylnaphthalene

To a 2 liter round-bottomed flask equipped with condenser and a nitrogen inlet were added 98.3 grams (0.552 mol) 4-(p-tolyl)butyric acid and 900 mL dry benzene. After the acid had dissolved, 132.6 mL (0.939 mol) trifluoroacetic anhydride was added dropwise over 35 minutes. The reaction was then refluxed for 20 hours (starting material confirmed to be consumed by thin layer chromatography (tlc), $R_f$ 0.1 to 0.6 (DNP+ve) in 2/1 ethyl acetate (EtOAc)/hexane) cooled, and evaporated to remove most of the trifluoroacetic acid. The reside was taken up in ethyl acetate, washed with dilute aqueous ammonium hydroxide, water and brine, dried over sodium sulfate, and evaporated. The resulting solid was suitable for use in the next step.

$^1$H NMR ($\delta$, CDCl$_3$): 2.46 (s, 3H), 2.54 (s, 3H), 7.2–7.4 and 7.6–7.8 (m, 6H).

$^{13}$C NMR (6, CDCl$_3$): 21.0, 22.0, 118.2, 120.0, 124.5, 125.8, 127.0, 128.0, 128.8, 133.1, 136.3, 146.2, 169.5.

C. 4-Phenyl-7-methyl-1-tetralone

To a 250 mL round-bottomed flask equipped with condenser and a nitrogen inlet were added 60 mL ethanol and 8.28 grams (148 mmol) powdered potassium hydroxide. After cooling, a solution of 8.0 grams (40 mmol) 1-acetoxy-7-methylnaphthalene in 50 mL ethanol was added, and the reaction stirred at room temperature for 1.2 hours (tlc $R_f$ 0.6 to 0.3 (potassium permanganate (KMnO$_4$)+ve) in 5/1 hexane/ethyl acetate). The reaction was evaporated to a small volume, taken up in methylene chloride/water, seperated, and the aqueous layer washed again with methylene chloride. The aqueous layer was adjusted to pH with 6N hydrochloric acid and extracted into ethyl acetate. The organic layer washed with brine, dried over sodium sulfate, and evaporated to a tan solid.

$^1$H NMR ($\delta$, CDCl$_3$): 2.52 (s, 3H), 6.80 (m, 1H), 7.2–7.4 (m, 3H), 7.71 (m, 1H), 7.98 (d, J=1, 1H).

MS (%): 158 (100, parent), 129 (23), 115 (18).

The solid was taken up in 100 mL dry benzene to which was added 11.18 grams (84 mmol) aluminum chloride, and the reaction heated to 60° C. for 2 hours (tlc $R_f$ 0.3 to 0.5 in 8/1 hexane/ethyl acetate). The reaction was cooled, poured over ice/water and extracted into ethyl acetate. The organic layer was washed with brine, dried over sodium sulfate, and evaporated. The residue was adsorbed onto silica gel and chromatographed using 5/1 hexane/ethyl acetate to give 7.4 grams (78%) of an oil.

$^1$H NMR ($\delta$, CDCl$_3$): 2.27 (m, 1H), 2.36 (s, 3H), 2.43 (m, 1H), 2.59 (m, 1H), 2.66 (m, 1H), 2.24 (m, 1H), 6.85 (d, J=8, 1H), 7.10 (m, 2H), 7.2–7.4 (m, 4H), 7.90 (d, J=1, 1H).

D. 2-Oxo-5-phenyl-2,3,4,5-tetrahydro-1H-(1)benzazepine

To a 250 mL round-bottomed flask equipped with condenser and a nitrogen inlet were added 7.4 grams (31.4 mmol) 4-phenyl-7-methyl-1-tetralone, 100 mL methanol, 6.56 mL (47.0 mmol) triethylamine, and 3.25 grams (47.0 mmol) hydroxylamine hydrochloride. The reaction was refluxed 24 hours (tlc $R_f$ 0.5 in 3/1 hexane/ethyl acetate), cooled, and evaporated. The residue was taken up in ethyl acetate and water, the layers separated, and the organic layer washed with dilute hydrochloric acid and brine, dried over sodium sulfate, and evaporated to an oil which solidified on standing.

$^1$H NMR ($\delta$, CDCl$_3$): 2.0–2.2 (m, 2H), 2.34 (s, 3H), 2.79 (t, J=6, 2H), 4.10 (m, 1H), 6.81 (d, J=8, 1H), 7.06 (m, 2H), 7.27 (m, 4H), 7.78 (bs, 1H).

The oxime was dissolved in 200 mL 1,2-dichloroethane, treated with 80 mL ethyl polyphosphate, and heated quickly to and held at 90°–105° C. for 40 minutes (tlc $R_f$ 0.05 in 3/1 hexane/ethyl acetate and 0.3 in 2/1 ethyl acetate/hexane), cooled, treated with 100 mL water, and stirred at room temperature for 20 hours. The layers were separated, the aqueous layer washed with methylene chloride, and the combined organic layers washed with water, dried over sodium sulfate, and evaporated. The residue was triturated with ether to a white solid, M.P. 230°–233° C., 5.48 grams (70%).

$^1$H NMR ($\delta 6$, CDCl$_3$): 2.23 (s, 3H), 2.4–2.6 (m, 2H), 2.85 (bs, 1H), 4.25 (m, 1H), 6.58 (d, J=8, 1H), 6.78 (m, 2H), 7.2–7.4 (m, 5H).

E. 3-Bromo-2-oxo-5-phenyl-2,3,4,5-tetrahydro-1H-(1)benzazepine

To a 200 mL three neck round-bottomed flask equipped with a nitrogen inlet and septum were added 5.48 grams (21.8 mmol) 5-phenyl-8-methyl-2-oxobenzazepine, 100 mL dichloromethane, and 4.55 grams (21.8 mmol) phosphorus pentachloride. After dissolution, 1.85 mL (22.9 mmol) pyridine was added, and the solution cooled to −70° C. To the stirring solution (some precipitate appeared at this temperature, but did not affect the reaction) was added a solution of 1.12 mL (21.8 mmol) bromine in 10 mL methylene chloride dropwise over 20 minutes. The reaction was then allowed to warm quickly (10 minutes) to 0° C., and 50 mL of saturated aqueous sodium bisulfite solution was added. The reaction was then diluted with methylene chloride and allowed to stand under sodium bisulfite solution with periodic shaking for 2 hours, until the organic phase no longer exhibited a reddish color. The organic phase was then dried over sodium sulfate and evaporated. The residue was suspended in methylene chloride and filtered, and the solid dissolved to afford 3.39 grams (47%) of product as a white solid. The filtrate was adsorbed onto silica gel and chromatographed using 7:3 hexane/ethyl acetate as eluant to afford additional product as a white solid, 1.38 g, total 5.14 (71%).

$^1$H NMR (δ, CDCl$_3$): 2.24 (s, 3H), 2.85 (m, 1H), 3.05 (m, 1H), 4.35 (m, 1H), 4.57 (m, 1H), 6.57 (d, J=8, 1H), 6.82 (m, 2H), 7.2–7.4 (m, 5H). This product has the cis stereochemistry.

F. N-tert-butyl-1–2-(3-bromo-2-oxo-5-phenyl-2,3,4,5-tetrahydro-1H-(1)benzazepin-1-yl) ethanoic acid amide To a 200 mL 3N round-bottomed flask equipped with a nitrogen inlet and septum were added 6.14 grams (18.6 mmol) 3-bromo–2-oxo-5-phenyl-2,3,4,5-tetrahydro-1H-(1)benzazepine and 80 mL tetrahydrofuran. The suspension was cooled to −70° C., and 20.5 mL (20.5 mmol) of a 1.0M solution of sodium hexamethyldisilazide in tetrahydrofuran was added over 5 minutes. The suspension was allowed to warm to 0° C. over 15 minutes to effect solution, then cooled to −70° C., and a solution of 4.93 grams (20.5 mmol) of t-butyliodoacetamide in 15 mL tetrahydrofuran was added dropwise over 10 minutes. The reaction was removed from the dry ice bath, and 50 mL dimethylsulfoxide added (most of which froze on contact). The reaction was warmed and stirred at room temperature for 14 hours (tlc R$_f$ 0.15 to 0.10 in 4/1 hexane/ethyl acetate), then poured into water and extracted into ethyl acetate. The organic layer was washed with several portions of water, sodium bisulfite solution and brine, dried over sodium sulfate and evaporated. The crude solid which precipitated from the ethyl acetate near the end of evaporation, 8.4 grams (theoretical 8.24 g), was used without further purification.

$^1$H NMR (δ, CDCl$_3$): 1.33 (s, 9H), 2.27 (3H), 2.82 (m, 1H), 2.95 (m, 1H), 4.35 (m, 2H), 4.56 (m, 2H), 6.14 (bs, 1H), 6.54 (d, J=8, 1H), 6.86 (d, J=8, 1H), 7.10 (bs, 1H), 7.2–7.4 (m, 5H). This product has the trans stereochemistry.

G. N-tert-butyl-2-(3-azido-2-oxo-5-phenyl-2,3,4,5-tetrahydro-1H-(1)benzazepin-1-yl)ethanoic acid amide To a 125 ml round-bottomed flask equipped with a nitrogen inlet were added 8.2 grams (18.5 mmol) N-tert-butyl 2-(3-bromo-2-oxo-5-phenyl-2,3,4,5-tetrahydro-1H-(1)benzazepin-1-yl) ethanoic acid amide and 40 ml dimethylformamide. After dissolution, a solution of 1.44 grams (22.2 mmol) sodium azide in 2 mL water (with two additional 0.75 ml portions of water) was added, and the solution heated at 80°–85° C. for 4 hours 20 minutes (at this point, tlc and NMR of an aliquot indicated a 75/15/10 ratio of desired azide/isomeric azide/starting material). The reaction was cooled, poured into water, and extracted twice into ethyl acetate. The organic layer was washed with water and brine, dried over sodium sulfate and evaporated. The residue was chromatographed on silica gel using 3:1 hexane/ethyl acetate to give 5.80 grams (77%) of a foam which solidified.

$^1$H NMR (δ, CDCl$_3$): (cis isomer) 1.28 (s, 9H), 2.33 (s, 3H), 2.75 (m, 1H), 2.92 (m, 1H), 3.04 (AB$_q$, J$_{AB}$=15, ΔV=274), 3.94 (m, 1H), 6.10 (bs, 1H), 7.0–7.3 (m, 8H).

H. N-tert-butyl-2-(3-amino-2-oxo-5-phenyl-2,3,4,5-tetrahydro-1H-(1)benzazepin-1-yl) ethanoic acid amide A solution of 5.80 grams (14.3 retool) N-tert-butyl-2-(3-azido-2-oxo-5-phenyl-2,3,4,5-tetrahydro-1H-(1)benzazepin-1-yl) ethanoic acid amide in 70 mL ethanol (with methylene chloride as necessary to aid dissolution) was treated with 600 mg 10% palladium on carbon under hydrogen (42 to 39 psi) for 20.5 hours. The reaction was filtered through Celite® with ethanol and methylene chloride and evaporated to a foam, 5.44 grams (100%).

$^1$H NMR (δ, CDCl$_3$) 1.28 (s, 9H), 2.29 (s, 3H), 2.67 (m, 1H), 2.81 (m, 1H), 3.04 (AB$_q$, J$_{AB}$=15, Δv=269), 3.34 (bs, 2H), 3.6 (m, 1H), 4.10 (m, 1H), 7.0–7.3 (m, 8H).

PREPARATION B

3-Tetrazolylbenzoic acid

To a 500 mL round-bottomed flask equipped with condenser and nitrogen inlet were added 10 grams (68 mmol) 3-cyano benzoic acid and 225 mL methanol. To the stirring solution was added 7 mL acetyl chloride carefully, and the reaction heated at 55° C. for 12 hours, then stirred at room temperature overnight. The reaction was concentrated, partitioned between water and ethyl acetate, washed with aqueous sodium bicarbonate, water, and brine, and dried over sodium sulfate. After evaporation, the residue was crystallized from isopropanol to give 8.32 grams (76%).

$^1$H-NMR (δ, CDCl$_3$): 3.93 (s, 3H), 7.56 (t, J=7, 1H), 7.82 (m, 1H), 8.23 (m, 1H), 8.30 (m, 1H).

IR (neat, cm$^{-1}$): 2228 (CN) cm.$^{-1}$.

The nitrile, 3.4 grams (21 mmol), was dissolved in 50 mL xylene, treated with 11.0 grams (52.7 mmol) of trimethylstannyl azide, and refluxed 3 hours. The reaction was cooled, poured into 5 N hydrochloric acid, shaken vigorously after addition of ehtyl acetate, and the organic layer separated and washed with water and brine. After drying over sodium sulfate and evaporation, the residue (particle beam Mass Spectroscopy showed P=205 for parent+1 peak, IR showed no peak at 2228 cm.$^{-1}$) was taken up in 30 mL tetrahydrofuran and treated with a solution of 1.04 grams (24.84 mmol) lithium hydroxide in 15 mL water and then enough methanol (8 mL) to give a solution. After stirring at room temperature for 20 hours, the reaction was concentrated, partitioned between ethyl acetate and 1N hydrochloric acid. The organic layer was washed with water and brine, dried over sodium sulfate, and evaporated to a white solid, 1.7 grams (91%).

$^1$H-NMR (δ, CDCl$_3$): 7.70 (t, J=8, 1H), 8.22 (m, 2H), 8.69 (bs, 1H).

IR (neat, cm.$^{-1}$): 1671 (C=O) cm.$^{-1}$.

MS (particle beam, %): 208 (parent+NH$_4^+$, 100), 191 (parent+1, 20).

EXAMPLE 1 cis,cis-N-tert-Butyl-2-[3-((3-(N-methanesulfonyl)carboxamidophenyl)ureido)-2-oxo-5-(2-methylphenyl)-7-phenyl-2,3,4,5,6,7-hexahydroazepin-1-yl]ethanoic acid amide A. 4-(2-Methylphenyl)-4-hydroxycyclohexanone ethylene ketal Prepared in analogy with *J. Med. Chem.*, 35, 320–324 (1992) as follows: To a 1 L round-bottomed flask equipped with nitrogen inlet were added 78.1 grams (0.50 mol) cyclohexane-1,4-dione monoethylene ketal and 500 mL dry tetrahydrofuran. The solution was cooled to −78° C., and 250 mL of a 2.0M solution (0.50 mol) of 2-methylphenylmagnesium bromide in ether was added dropwise over 30 minutes, then the reaction was stirred for 10 minutes and warmed to room temperature. The reaction was poured into ice/water, the layers separated, and the aqueous phase extracted with ether. The combined organic phase was dried over sodium sulfate and evaporated to a an oil, which was used directly in the next step.

$^1$H-NMR (δ, CDCl$_3$): 1.5–2.4 (m, 8H), 2.64 (s, 3H), 3.9–4.1 (m, 4H), 7.1 (m, 3H), 7.45 (m, 1H).

MS (%): 230 (25, parent-H$_2$O), 129 (15), 101 (30), 86 (100).

B. 4-(2-Methylphenyl)cyclohexanone

A solution of 4-(2-methylphenyl)-4-hydroxycyclohexanone ethylene ketal from the preceding step in 800 mL dioxane was treated with 16 mL concentrated hydrochloric acid and 30 grams 10% palladium-on-carbon under 35 p.s.i.

hydrogen for 24 hours, then filtered through Celite® to remove the catalyst. The filtrate was treated with 230 mL water and stirred at room temperature for 48 hours. The solution was evaporated, the pH adjusted to 8 with saturated aqueous sodium bicarbonate solution, and extracted with methylene chloride. The organic layer was dried over sodium sulfate and evaporated. The residue was chromatographed on silica gel using ethyl acetate/hexane as eluant to afford 33.3 grams (35%) of an oil.

$^1$H-NMR ($\delta$, CDCl$_3$): 1.9 (m, 2H), 2.12 (m, 2H), 2.39 (s, 3H), 2.49 (m, 4H), 3.21 (triplet of triplets, J=4,12, 1H), 7.1–7.2 (m, 4H).

MS (%): 188 (60, parent), 131 (65), 118 (100).

C. 2-Chloro-4-(2-methylphenyl)cyclohexanone

Prepared in analogy with a method in Hussey, A. S. and Herr, R. R., *J. Org. Chem.*, 24, 843 (1959). To a 500 mL round-bottomed flask equipped with nitrogen inlet were added 33.3 grams (0.177 tool) of 4-(2-methylphenyl)cyclohexanone and 200 mL methylene chloride. To the stirring solution was added dropwise over 30 minutes a solution of 17.1 mL (0.212 mol) sulfuryl chloride in 10 mL methylene chloride. The reaction was stirred 14 hours at room temperature and poured into saturated aqueous sodium bicarbonate solution. The organic layer was separated, washed again with saturated aqueous sodium bicarbonate solution, dried over sodium sulfate, and evaporated to a yellow oil, 41 grams (100%), as a mixture of diastereomers which was used directly in the next step.

$^1$H-NMR ($\delta$, CDCl$_3$): 1.9–2.7 (m, 6H), 2.42 and 2.44 (singlets, for each diastereomer, 3H), 3.2 (m, 1H), 4.68 and 5.36 (multiplets, 1H), 7.1–7.2 (m, 4H).

MS (%): 222 (80, parent), 159 (65), 118 (100), 105 (55), 55 (50).

D. 2-Phenyl-4-(2-methylphenyl)cyclohexanone

The above oil was dissolved in 200 mL dry benzene and added dropwise over 40 minutes to 59 mL (177 mmol) of a 3.0M solution of phenylmagnesium bromide in ether, cooling so the temperature did not rise above 10° C. The reaction was then allowed to warm and heated to reflux for 16 hours. It was then cooled, quenched with aqueous ammonium chloride solution, then washed with water and brine, dried over sodium sulfate, and evaporated. The residue was chromatographed on silica gel using hexane/ethyl acetate as eluant to afford a tan oil, 13.1 grams (28%). The oil, which is only the cis diastereomer, was used directly in the next step.

$^1$H-NMR ($\delta$, CDCl$_3$): 2.0–2.6 (m, 4H), 2.44 (s, 3H), 2.70 (m, 2H), 3.49 (m, 1H), 3.83 (dd, J=5,13, 1H), 7.0–7.4 (m, 9H).

MS (%): 264 (75, parent), 160 (70), 118 (100), 91 (80).

E. 2-phenyl-4-2-methylphenyl)cyclohexanone oxime 2-phenyl-4-(2-methylphenyl)cyclohexanone, 13.1 grams (49.5 mmol), was dissolved in 200 mL methanol/methylene chloride, followed by 11.1 mL (79.3 mmol) triethylamine and 5.5 grams (79.3 mmol) hydroxylamine hydrochloride. The solution was stirred at room temperature for 48 hours, the solvent evaporated, and the resulting solid washed with methanol and dried to afford 8.2 grams (59%) of a yellow solid.

$^1$H-NMR (6, CDCl$_3$): 1.7–2.2 (m, 4H), 2.39 (s, 3H), 3.0–3.2 (m, 2H), 3.58 (m, 2H), 7.0–0.74 (m, 9H), 8.25 (bs, 1H), OH).

$^{13}$C-NMR ($\delta$, CDCl$_3$): 19.4, 24.8, 31.9, 39.4, 40.7, 49.6, 125.1, 126.1, 126.4, 126.8, 128.3, 128.6, 130.5, 135.2, 140.1, 143.3, 161.1.

F. 5-(2-Methylphenyl)-7-phenyl-2,3,4,5,6,7-hexahydroazepin-2-one

To a 250mL round-bottomed flask equipped with nitrogen inlet were added 8.20 grams (29.4 mmol) 2-phenyl-4-(2-methylphenyl)cyclohexanone oxime and 80 mL pyridine. Once the solid had dissolved, the solution was cooled to 0° C., and 27.9 grams (147 mmol) p-toluenesulfonyl chloride was added. The reaction was allowed to stir for 16 hours while the ice bath melted and the reaction warmed to room temperature. It was then poured into 300 mL 3N HCl, extracted into ethyl acetate, and the organic layer washed with additional hydrochloric acid and brine, dried over sodium sulfate, and evaporated. The residue was chromatographed on silica gel using methanol/methylene chloride as eluant to afford 5.27 grams (64%) of an amorphous solid.

$^1$H-NMR ($\delta$, CDCl$_3$): 1.8–2.2 (m, 4H), 2.33 (s, 3H), 2.70 (m, 2H), 3.15 (m, 1H), 4.60 (m, 1H), 5.74 (bs, 1H), N$\underline{H}$), 7.0–7.4 (9H).

G. 3-Bromo-5-(2-methylphenyl-7-phenyl-2,3,4,5,6,7-hexahydroazepin-2-one

To a 250 mL round-bottomed flask equipped with addition funnel and nitrogen inlet were added 3.5 grams (16.8 mmol) phosphorus pentachloride and 25 mL dry methylene chloride. The mixture was cooled with stirring to 0° C., and a solution of 4.7 grams (16.8 mmol) 5-(2-methylphenyl)-7-phenyl-2,3,4,5,6,7-hexahydroazepin-2-one and 2.7 mL (33.6 mmol) pyridine in 50 mL methylene chloride was added dropwise over 20 minutes. The reaction was stirred 5 minutes at 0° C., then 1.9 mL (37.0 mmol) bromine in 5 mL methylene chloride was added dropwise over 5 minutes. The reaction was stirred 5 minutes at 0° C., then 1.8 hours at room temperature. The reaction was evaporated, taken up in 40 mL of 1:1 tetrahydrofuran:water, and stirred for 1.2 hours. The reaction was then poured into water and extracted into ethyl acetate. The organic layer was washed with aqueous sodium bisulfite solution and brine, dried over sodium sulfate, and evaporated to an oil. At this point, a little of the desired monobrominated product can be recovered by chromatography, as described below; the remainder, mostly dibromo adduct, is treated as follows.

The oil was taken up in 20 mL methylene chloride and 20 mL ethanol, and hydrogenated under 42 psi hydrogen in the presence of 0.70 grams 10% palladium-on-carbon and 7 drops of quinoline for 1 hour. Tlc showed mostly desired monobromo product at R$_f$=0.5, with a little dibromo precursor at R$_f$=0.7 and starting lactam at R$_f$=0.15, in 1/1-ethyl acetate/hexane. The reaction was filtered through Celite with ethanol and methylene chloride, evaporated, and chromatographed on silica gel using 2/1-hexane/ethyl acetate as eluant to afford 2.8 grams (46%) of a foam, a mixture of diastereomers.

$^1$H-NMR ($\delta$, CDCl$_3$): 2.1–2.5 (m, 4H), 2.35 and 2.39 (singlets, 3H), 3.40 and 3.84 (multiplets for the diastereomers at the 5-position, 1H), 4.81 and 5.05 (multiplets for the diastereomers at the 3-position, 1H), 5.83 and 5.93 (bs's, 1H) N$\underline{H}$), 7.1–7.4 (m, 9H).

FAB MS: 358/360 (parent for Br$^{79}$/Br$^{81}$), 280 (100).

H. N-(t-Butyl-2-oxo-3-bromo-5-(2-methylphenyl)-7-phenyl-2,3,4,5,6,7-hexahydroazepin-1-yl ethanoic amide To a 1000 mL 3-necked round-bottomed flask equipped with addition funnel and nitrogen inlet were added 3.9 grams (97.6 mmol) sodium hydride, which was then washed with hexane, and 400 mL dry tetrahydrofuran. To the stirring suspension was added a solution of 31.8 grams (88.8 mmol) 3-bromo-5-(2-methylphenyl)-7-phenyl-2,3,4,5,6,7-hexahydroazepin-2-one and 23.5 grams (97.6 mmol) t-butyl iodoacetamide. The reaction was stirred at room temperature for 60 hours, quenched with ammonium chloride solution, then poured into water, extracted twice into ethyl acetate, washed with brine, dried over sodium sulfate, and evaporated. The residue was chromatographed on silica gel using 2/1-hexane/ethyl acetate as eluant to afford 38.7 grams (92%) of a foam, a mixture of diastereomers.

$^1$H-NMR (δ, CDCl$_3$): 1.27 and 1.29 (singlets for the two diastereomers, 9H), 2.0–2.6 (m, 4H), 2.32 and 2.36 (s's, 3H), 3.2–3.9 (m, 4H), 5.0–5.6 (m, 2H), 6.9–7.3 (m, 9H).

$^{13}$C-NMR (δ, CDCl$_3$): 19.5, 27.3, 28.4, 28.7, 38.0, 39.2, 39.7, 41.7, 41.9, 49.0, 50.7, 51.1, 51.2, 59.4, 61.8, 62.2, 126.1, 126.3, 126.6, 126.7, 128.3, 128.5, 128.7, 129.0, 129.4, 130.6, 135.0, 139.5, 142.7, 167.6, 170.0, 170.5.

I. N-(t-Butyl)-2-oxo-3-azido-5-2-methylphenyl)-7-phenyl-2,3,4,5,6,7-hexahydroazepin-1-yl ethanoic amide To a 250 mL round-bottomed flask equipped with nitrogen inlet were added 38.7 grams (82.1 mmol) N-(t-butyl)-2-oxo-3-bromo-5-(2-methylphenyl)-7-phenyl-2,3,4,5,6,7-hexahydroazepin-1-yl ethanoic amide, 150 mL dry dimethylformamide, and 6.4 grams (98.5 mmol) sodium azide. The reaction was heated at 80° C. for 3.5 days, cooled, poured into water, and extracted into ethyl acetate. The organic layer was washed with water and brine, dried over sodium sulfate, and evaporated. The residue was chromatographed on silica gel using 40% ethyl acetate in hexane as eluant to afford 13.8 grams (38%) of an oil, the more polar spot which was found to be the desired cis diastereomer, $R_f$=0.6 in 1/1-ethyl acetate/hexane.

$^1$H-NMR (δ, CDCl$_3$): 1.285 (s, 9H), 2.2 (m, 2H), 2.33 (s, 3H), 2.7 (m, 1H), 3.3–3.5 (2H), 3.60 (AB$_q$, J$_{AB}$=15, Δv=215, 2H), 4.55 (m, 1H), 4.95 (m, 1H), 5.60 (bs, 1H), 7.1–7.5 (m, 9H).

13C-NMR (δ, CDCl$_3$): 19.5, 28.7, 36.8, 38.1, 41.1, 48.4, 51.1, 61.2, 61.5, 126.1, 126.7, 128.8, 129.4, 130.7, 134.3, 137.9, 142.6, 167.6, 172.4.

IR (KBr, cm.$^{-1}$): 2110 (N$_3$), 1660 (C=O).

FAB Mass Spectroscopy (%): 434 (28 (parent+1), 408 (55), 207 (68), 105 (64), 91 (100).

J. N-(t-Butyl)-2-oxo-3-amino-5-(2-methylphenyl)-7-phenyl-2,3,4,5,6,7-hexahydroazepin-1-yl ethanoic amide A solution of 13.7 grams (31.6 mmol) N-(t-butyl)-2-oxo-3-azido-5-(2-methylphenyl)-7-phenyl-2,3,4,5,6,7-hexahydroazepin-1-yl ethanoic amide in 120 mL ethanol and 60 mL methylene chloride was hydrogenated at 42 psi in the presence of 3.9 grams 10% palladium-on-carbon for 36 hours. The reaction showed $R_f$=0.30/0.15 iodoplatinate positive, in 30% methanol in ethyl acetate. It was filtered through Celite with ethanol and methylene chloride, evaporated, and chromatographed on silica gel using 15% and 30% methanol in ethyl acetate as eluant to afford 12.2 grams (95%) of a foam. $^1$H-NMR (δ, CDCl$_3$): 1.13 (singlet, 9H), 2.0–2.5 and 3.9 (multiplets, 6H), 2.28 (s, 3H), 3.4 (m, 1H), 4.7 (m, 2H), 5.18 (d, J=10, 1H), 5.94 (broad singlet, 1H, NH), 7.0–7.3 (m, 9H). $^{13}$C-NMR (δ, CDCl$_3$): 19.6, 28.6, 37.3, 38.7, 40.8, 48.2, 51.1, 53.5, 60.9, 126.0, 126.4, 128.6, 128.8, 129.8, 130.6, 134.8, 138.1, 143.0, 168.0, 174.1.

K. Cis, cis-N-tert-Butyl-2-[3-((3-carbomethoxyphenyl)ureido)-2-oxo-5-(2-methylphenyl)-7-phenyl-2,3,4,5,6,7-hexahydroazepin-1-yl]ethanoic acid amide To a 35 mL round-bottomed flask equipped with nitrogen inlet and condenser were added 62 mg (0.382 mmol) 3-carbomethoxybenzoic acid, 5 mL dry tetrahydrofuran, 0.090 mL (0.420 mmol) diphenylphosphoryl azide, and 0.060 mL (0.420 mmol) triethylamine. The reaction was refluxed for 1 hour, cooled briefly, and 150 mg (0.382 mmol) of N-(t-butyl)-2-oxo-3-amino-5-(2-methylphenyl)-7-phenyl-hexahydroazepin-1-yl ethanoic amide (the more polar isomer from the preceding example) was added and refluxing continued for 14 hours. The reaction was cooled, filtered to remove a small amount of amide by product that had formed, and the filtrate evaporated. The residue was chromatographed on silica gel using hexane/ethyl acetate as eluant to afford a white foam, 481 mg (69%), which was used directly in the next step.

$^1$H-NMR (δ, CDCl$_3$): 1.18 (s, 9H), 2.12 (m, 3H), 2.30 (s, 3H), 2.60 (m, 1H), 3.43 (m, 1H), 3.61 (AB$_q$, J$_{AB}$=16, Δv=229), 3.80 (S, 3H), 5.24 (m, 2H), 6.8–8.0 (m, 16H).

FAB Mass Spectroscopy (%): 585 (parent+1, 22), 512 (44), 207 (100).

Anal. Calc'd. for C$^{34}$H$_{40}$N$_4$O$_5$·½H$_2$O: C. 68.78, H 6.96, N 9.44. Found: C. 69.02, H 6.84, N 9.22.

L. cis,cis-N-tert-Butyl-2-[3-((3-carboxyphenyl)ureido)-2-oxo-5-(2-methylphenyl)-7-phenyl-2,3,4,5,6,7-hexahydroazepin-1-yl]ethanoic acid amide To a 100 mL round-bottomed flask equipped with nitrogen inlet were added 433 mg (0.74 mmol) cis,cis-N-tert-butyl-2-[3-((3-carbomethoxyphenyl)ureido)-2-oxo-5-(2-methylphenyl-7-phenyl-2,3,4,5,6,7-hexahydroazepin-1-yl] ethanoic acid amide and 8 mL tetrahydrofuran. To the stirring solution was added a solution of 156 mg (3.7 mmol) lithium hydroxide hydrate in 4 mL water, followed by 4 mL methanol to give a solution. The reaction was stirred for 2.5 days at room temperature, poured into 0.5N hydrochloric acid, and the precipitate collected. This white solid was chromatographed on silica gel using methanol/ethyl acetate as eluant to afford 259 mg (59%) yield of a white solid, M.P. 185° C. (dec.).

$^1$H-NMR (δ, CDCl$_3$): 1.30 (s, 9H), 2.05 (m, 1H), 2.30 (m, 2H), 2.41 (s, 3H), 2.65 (m, 1H), 3.60 (m, 1H), 3.64 (AB$_q$, J$_{AB}$=16, Δv=191), 5.30 (m, 2H), 7.0–8.5 (m, 16H).

$^{13}$C-NMR (δ, CDCl$_3$): 19.6, 28.7, 37.6, 39.3, 41.1, 48.6, 51.4, 52.5, 53.4, 62.0, 119, 122.4, 126.0, 126.0, 126.4, 128.9, 129.1, 129.2, 129.5, 129.7, 130.5, 134.9, 137.8, 140.7, 143.1, 154.6, 166.8, 170.0, 175.4.

IR (cm.$^{-1}$KBr): 1670 (CO$_2$H) and 1640 (CONR).

FAB Mass Spectroscopy (%): 571 (parent1, 17), 498 (37), 207 (100).

Anal. Calc'd. for C$_{33}$H$_{38}$N$_4$O$_5$·¾H$_2$O: C 67.85, H 6.82, N 9.59. Found: C 67.99, H 6.78, N 9.22.

M. cis,cis-N-tert-Butyl-2-[3-((3-(N-methanesulfonyl)carboxamidophenyl)-ureido)-2-oxo-5-(2-methylphenyl)-7-phenyl-2,3,4,5,6,7-hexahydroazepin-1yl]ethanoic acid amide To a 100 mL round-bottomed flask equipped with nitrogen inlet were added 100 mg (0.18 mmol) cis,cis-N-tert-butyl-2-[3-((3-carboxyphenyl)ureido)-2-oxo-5-(2-methylphenyl)-7-phenyl-2,3,4,5,6,7-hexahydroazepin-1-yl] ethanoic acid amide, 18 mg (0.19 mmol) methanesulfonamide, 37 mg (0.19 mmol) 1-ethyl-3-(3-dimethylaminopropyl)-carbodiimide, 24 mg (0.19 mmol ) 4-dimethylaminopyridine, and 6 mL methylene chloride. The reaction was stirred at room temperature for 18 hours, then chromatographed on silica gel using methanol/methylene chloride as eluant to afford the product, $R_f$=0.4 in 10% methanol/methylene chloride, 35 mg (30%), M.P. 175° C. (dec.).

$^1$H-NMR (δ, CDCL$_3$): 1.19 (s, 9H), 2.10 (m, 3H), 2.35 (s, 3H), 2.65 (m, 1H), 3.30 (s, 3H), 3.65 (m, 1H), 3.73 (AB$_q$, J$_{AB}$=17, Δv=189), 5.20 (m, 1H), 5.35 (m, 1H), 6.9–7.6 (m, 15H), 8.04 (bs, 1H, NH).

$^{13}$C-NMR (δ, CDCl$_3$): 19.7, 29.0, 39.9, 40.0, 42.1, (methanol obscures peaks in this region), 52.0, 53.7, 62.3, 119.7, 123.2, 124.4, 127.1, 127.3, 127.5, 129.6, 130.0, 130.2, 130.8, 131.5, 135.9, 140.2, 141.5, 145.0, 156.9, 170.0, 175.8 (one C=O signal too weak for observation).

IR (cm.$^{-1}$, KBr): 1740 (CO$_2$R) and 1640 (CONR).

FAB Mass Spectroscopy (%): 648 (parent+1, 10), 486 (12), 309 (14), 155 (52), 119 (100).

HRMS: Calc'd. for C$^{34}$H$_{42}$N$_5$O$_6$S (P+1): 648.2856. Found: 648.2913.

EXAMPLE 2 cis,cis-N-tert-Butyl-2-[3-((N-benzenesulfonyl)carboxamidophenyl)ureido)-2-oxo-5-(2-methylphenyl)-7-phenyl-2,3,4,5,6,7-hexahydroazepin-1yl]ethanoic acid amide Prepared in analogy with Example 1M using benzenesulfonamide in 62% yield, M.P. 110° C. (dec.).

FAB Mass Spectroscopy (%): 710 (parent+1, 13), 637 (20), 207 (100), 155 (41), 119 (85).

Anal. Calc'd. for C$_{39}$H$_{43}$N$_5$O$_6$S. ⅝H$_2$CO$_3$: C 61.40, H 5.82, N 8.89. Found: C 61.17, H 5.88, N 9.01.

EXAMPLE 3 cis,cis-N-tert-Butyl-2-[3-((N-benzylsulfonyl)carboxamidophenyl)ureido)-2-oxo-5-(2-methylphenyl)-7-phenyl-2,3,4,5,6,7-hexahydroazepin-1-yl]ethanoic acid amide Prepared in analogy with Example 1M using benzylsulfonamide in 81% yield, M.P. 185° C. (dec.).

FAB Mass Spectroscopy (%): 724 (parent+1, 3), 155 (74), 135 (76), 119 (100).

Anal. Calc'd. for C$_{40}$H$_{45}$N$_5$O$_6$S.½H$_2$CO$_3$: C 64.44, H 6.14, N 9.28. Found: C 64.71, H 5.82, N 9.47.

EXAMPLE 4 cis,cis-N-tert-Butyl-2-[3-[3-(3-(N-2-tolylsulfonyl)carboxamidophenyl)ureido)2-oxo-5-(2-methylphenyl)-7-phenyl-2,3,4,5,6,7-hexahydroazepin-1-yl]ethanoic acid amide Prepared in analogy with Example 1M using 2-tolylsulfonamide in 48% yield, M.P. 200° C. (dec.).

FAB Mass Spectroscopy (%): 724 (parent+1, 18.5), 762 (parent+K$^+$, 40), 746 (parent+Na$^+$, 70), 17e (100).

Anal. Calc'd. for C$^{40}$H$_{45}$N$_5$O$_6$S: C 66.37, H 6.27, N 9.67. Found: C 64.71, H 6.46, N 10.01.

EXAMPLE 5 cis,cis-N-tert-Butyl-2-[3-(3-(N-trifluoromethanesulfonyl)carboxamido-phenyl)ureido)-2-oxo-5-(2-methylphenyl)-7-phenylhexahydroazepin-1-yl]ethanoic acid amide Prepared in analogy with Example 1M using trifluoromethanesulfonamide in 44% yield, M.P. 250° C. (dec.).

FAB Mass Spectroscopy (%): 740 (parent+K$^+$, 100), 207 (55), 129 (50).

Anal. Calc'd. for C$_{34}$H$_{38}$F$_3$N$_5$O$_6$S. ¾H$_2$CO$_3$: C 55.78, H 5.32, N 9.36. Found: C 55.77, H 5.647, N 9.46.

EXAMPLE 6 cis,cis-N-tert-Butyl-2-[3-(3-(N-5-tetrazolyl)carboxamidophenyl)ureido)-2-oxo-5-oxo-5-(2-methylphenyl)-7-phenyl-2,3,4,5,6,7-hexahydroazepin-1-yl]ethanoic acid amide Prepared in analogy with Example 1M using 5-aminotetrazole in 33% yield, M.P. 310° C. (dec.).

FAB Mass Spectroscopy (%): 676 (parent+K$^+$, 17), 207 (100).

Anal. Calc'd. for C$^{34}$H$_{39}$N$_9$O$_4$.2H$_2$CO$_3$.¼H$_2$O: C 54.50, H 5.91, N 15.89. Found: C 54.30, H 5.61, N 16.27.

EXAMPLE 7 cis,cis-tert-Butyl-2-[3-(3-(N-5-(2-trifluoromethyl)-1,3,4-thiadiazolyl)carboxamidophenyl)ureido)-2-oxo-5-(2-methylphenyl)-7-phenylhexahydroazepin-1-yl]ethanoic acid amide Prepared in analogy with Example 1M using 5-trifluoromethyl-2-amino-3,4-thiadiazole in 37% yield, M.P. 180° C. (dec.).

FAB Mass Spectroscopy (%): 722 (parent+1, 1.5), 155 (83), 135 (85), 119 (100).

Anal. Calc'd. for C$^{36}$H$_{38}$F$_3$N$_7$O$_4$S: C 59.91, H 5.31, N 13.58. Found: C 59.95, H 5.47, N 12.95.

EXAMPLE 8 cis,cis-N-tert-Butyl-2-[3-(3-(N-2-thiazolyl)carboxamidophenyl)ureido)-2-oxo-5-(2-methylphenyl)-7-phenyl-2,3,4,5,6,7-hexahydroazepin-1-yl]ethanoic acid amide Prepared in analogy with Example 1M using 2-aminothiazole in 66% yield, M.P. 175° C. (dec.).

FAB Mass Spectroscopy (%): 653 (parent+1, 30), 207 (100).

Anal. Calc'd. for C$_{36}$H$_{40}$N$_6$O$_4$S.½H$_2$O: C 65.33, H 6.24, N 12.70. Found: C 65.56, H 6.17, N 12.70.

EXAMPLE 9

A. 5-(4-Tolyl), 5-cyclohexylbutyrolactone

To a 500 mL round-bottomed flask equipped with nitrogen inlet were added 26.67 grams (0.121 mol) ethyl 2-(4-toluyl)propionate (prepared by esterification of the corresponding acid, which was prepared by the method of *Org. Syn. Coll.* Vol. 2, 81 (1943)) and 275 mL dry tetrahydrofuran. The solution was cooled to 3° C., and a 2N solution of cyclohexyl magnesium chloride, 66 mL (0.133 mol), was added dropwise over 20 minutes. The reaction was then warmed to room temperature, and stirred for 3 hours. The reaction was poured into saturated aqueous ammonium chloride solution and extracted into ethyl acetate. The organic layer was washed with more ammonium chloride and brine, dried over sodium sulfate, and evaporated. The product gave R$_f$=0.25 compared to starting material at R$_f$=0.30 in 8:1 hexane:ethyl acetate on silica gel, and was used directly in the following step.

3-Cyclohexyl-3-(4-tolyl)butanoic acid

The resulting orange oil was dissolved in 121 mL trifluoroacetic acid, heated to reflux, and treated with 58 mL (0.364 mol) triethylsilane dropwise over 5 hours. Refluxing was continued for three days, and the reaction poured into water and extracted into ethyl acetate. The organic layer was washed with water and aqueous sodium bicarbonate solution, brine, dried over magnesium sulfate, filtered, and evaporated. The residue was taken up in aqueous sodium hydroxide solution, washed with ethyl acetate, then acidified with hydrochloric acid, extracted into ethyl acetate, dried, and evaporated. The resulting oil gave 17.94 grams (57%).

$^1$H-NMR (δ, CDCl$_3$): 0.6–2.4 (m, 16H), 2.28 (s, 3H), 6.9–7.2 (m, 4H).

MS (%): 260 (parent, 22), 177 (80), 131 (100), 55 (45), 41 (50).

B. 4-Cyclohexyl-7-methyl-1,2,3,4-tetrahydronaphth-1-one

To a 250 mL round-bottomed flask equipped with condenser and nitrogen inlet were added 31.52 grams (121 mmol) 3-cyclohexyl-3-(4-tolyl)butanoic acid, 76 mL benzene, and 29 mL (206 mmol) trifluoroacetic anhydride. The reaction was refluxed for 18 hours, cooled, and concentrated. The residue was partitioned between water and ethyl acetate. The organic phase was washed with water, 10% aqueous ammonium hydroxide solution, and water, then dried and evaporated. The oil was chromatographed on silica gel using hexane/ethyl acetate as eluant to afford an oil, 5.20 grams (18%).

$^1$H-NMR (δ, CDCl$_3$): 0.9–1.4 (m, 6H), 1.5–1.9 (m, 6H), 2.0–2.2 (m, 2H), 2.33 (s, 3H), 2.5–2.8 (m, 2H), 7.1 (m, 1H), 7.25 (m, 1H), 7.80 (s, 1H).

$^{13}$C-NMR (6, CDCl$_3$): 20.9, 24.4, 26.4, 26.5, 30.5, 31.9, 35.1, 40.0, 43.7, 127.5, 127.6, 129.1, 132.2, 133.5, 136.2, 144.4, 198.9.

IR (cm.$^{-1}$, KBr): 1682 (C=O).

MS (%): 242 (parent, 20), 160 (100).

HRMS: Calc'd. for C$_{17}$H$_{22}$O: 242.1665. Found: 242.16562.

C. 4-Cyclohexyl-7-methyl-1,2,3,4-tetrahydronaphth-1-one oxime

To a 125 mL round-bottomed flask equipped with condenser and nitrogen inlet were added 5.20 grams (21.49 mmol) 4-cyclohexyl 7-methyl-1,2,3,4-tetrahydronaphth-1-one, 54 mL methanol, 3.25 grams (32.23 mmol) triethylamine, and 2.22 grams (32.23 mmol) hydroxylamine hydrochloride. The reaction was stirred at room temperature for 1.5 days, evaporated, partitioned between ethyl acetate and water, and the aqueous layer extracted with fresh ethyl acetate. The combined organic layer was dried over sodium sulfate and evaporated to an oil, which was used directly.

$^1$H-NMR (δ, CDCl$_3$): 0.9–2.4 (m, 14H), 2.325 (s, 3H), 2.80 (m, 2H), 6.98 (m, 1H), 7.07 (m, 1H), 7.64 (s, 1H).

$^{13}$C-NMR (δ, CDCl$_3$): 20.4, 21.1, 22.5, 26.4, 31.0, 32.0, 38.9, 44.5, 124.9, 129.4, 129.5, 129.7, 136.0, 140.3, 155.9.

MS (%): 257 (parent, 15), 174 (100).

HRMS: Calc'd. for C$_{17}$H$_{23}$NO: 257.1776. Found: 257.17903.

D. 5-Cyclohexyl-8-methyl-2,3,4,5-tetrahydro-1H-(1)benzazepin-2-one

To a 250 mL round-bottomed flask equipped with nitrogen inlet were added 5.52 grams (21.48 mmol) 4-phenyl-6-methyl-1,2,3,4-tetrahydronaphth-1-one oxime, 140 mL 1,2-dichloroethane, and 55 grams ethylpolyphosphate. The mixture was heated in a 100° C. oil bath for 30 minutes, cooled, and water added and the mixture stirred overnight. The layers were separated, and the aqueous layer washed with methylene chloride. The combined organic layers were washed with water and brine, dried over sodium sulfate, and evaporated. The residue was chromatographed on silica gel using methylene chloride/ethyl acetate as eluant to afford 4.36 grams (79%) of a solid, M.P. 171°–173° C.

$^1$H-NMR (δ, CDCl$_{13}$): 0.6–2.0 (multiplets, 13H), 2.1–2.4 (m, 2H), 2.28 (s, 3H), 2.53 (m, 1H), 6.82 (s, 1H), 6.91 (m, 1H), 7.05 (m, 1H), 8.83 (s, 1H, N$\underline{H}$).

$^{13}$C-NMR (δ, CDCl$_3$): 20.8, 26.3, 26.4, 26.5, 31.0, 31.7, 32.5, 32.7, 38.8, 45.5, 123.0, 126.0, 128.4, 133.1, 136.7, 138.0, 176.3.

IR (cm.$^{-1}$, KBr): 1670 (C=O)

MS (%): 257 (parent, 30), 174 (100).

Anal. Calc'd. for C$_{17}$H$_{23}$NO: C. 79.33, H 8.96, N 5.38. Found: C 79.35, H. 8.96, N 5.38.

E. 3-Bromo-5-cyclohexyl-8-methyl-2,3,4,5-tetrahydro-1H-(1) benzazepin-2-one

To a 250 mL round-bottomed flask equipped with nitrogen inlet were added 4.36 grams (16.96 mmol) 5-cyclohexyl-8-methyl-2,3,4,5-tetrahydro-1H-(1) benzazepin-2-one, 46 mL methylene chloride, and 3.48 grams (16.96 mmol) phosphorus pentachloride. After dissolution, 1.44 mL (17.81 mmol) dry pyridine was added, and the reaction cooled to −78° C. Bromine, 2.71 mL (16.96 mmol), was added dropwise over 5 minutes, and the reaction stirred at −78° C. for 10 minutes, then warmed rapidly to 0° C., and quenched with saturated aqueous sodium bisulfite solution. After stirring for several hours, the layers were separated, and the aqueous layer washed with methylene chloride. The combined organic layers were washed with water and brine, dried, and evaporated. The residue was chromatographed on silica gel using methylene chloride/ethyl acetate to give 5.61 grams (~100%) of a foam, which was triturated with methylene chloride and hexane to give a solid, M.P. 124°–148° C., mixture of diastereomers.

$^1$H-NMR (δ, CDCl$_3$): 0.4–2.0 (m, 12H), 2.29 (s, 3H), 2.4–2.9 (m, 2H), 4.37 and 4.62 (multiplets, 1H, diastereomers), 6.9–7.1 (m, 3H), 8.67 and 8.82 (singlets, 1H, diastereomers).

$^{13}$C-NMR (δ, CDCl$_3$): 20.8, 26.1, 26.2, 26.3, 26.4, 30.3, 32.0, 32.1, 32.3, 38.0, 39.7, 42.7, 43.9, 45.0, 47.3, 48.2, 48.8, 123.6, 123.8, 126.7, 126.9, 127.2, 131.4, 132.2, 132.3, 135.9, 137.1, 137.2, 137.9, 169.7, 170.1.

IR (cm.$^{-1}$, KBr): 1670 (C=O).

MS (%): 336/338 (100/95, parent for Br$^{79}$/Br$^{81}$), 258 (75).

Anal. Calc'd. for C$_{17}$H$_{22}$BrNO: C. 61.05, H 6.59, N 4.16. Found: C 60.59, H 6.34, N 4.03.

HRMS: Calc'd. for C$_{17}$H$_{22}$BrNO: 335.0885. Found: 335.09019.

F. N-t-Butyl 2-[3-bromo-2-oxo-5-cyclohexyl-8-methyl-2,3,4,5,-tetrahydro-1H-(1)benzazepin-1-yl]ethanoic acid amide To a 125 mL round-bottomed flask equipped with nitrogen inlet were added 4.7 grams (13.97 mmol) 3-bromo-5-cyclohexyl-8-methyl-2,3,4,5-tetrahydro-1H-(1)benzazepin-2-one and 70 mL dry tetrahydrofuran. The solution was cooled to −78° C., and 16.8 mL (16.76 mmol) of a 1N solution of sodium bistrimethylsilylamide in tetrahydrofuran was added, followed by a solution of 4.04 grams (16.76 mmol) of t-butyl iodoacetamide in 35 mL dry tetrahydrofuran dropwise over 15 minutes. The reaction was stirred for 10 minutes, then warmed, 35 mL dry dimethylsulfoxide added, and the reaction stirred at room temperature for 14 hours. It was then poured into 1N hydrochloric acid, extracted into ethyl acetate, and the organic layer washed with water, saturated aqueous sodium bisulfite solution, brine, dried, and evaporated. The residue was chromatographed on silica gel with hexane/ethyl acetate to afford the two diastereomeric products, the less polar isomer, M.P. 183°–186° C., 2.16 g, 34% yield, and the more polar isomer, M.P. 206.5°–207.5° C., 3.16 g. 50% yield.

Less polar isomer (cis):

$^1$H-NMR (δ, CDCl$_{13}$): 0.4–2.0 (m, 14H), 1.36 (s, 9H), 2.305 (s, 3H), 2.36 (m, 1H), 2.59 (m, 2H), 4.05 (AB$_q$, J$_{AB}$=14, Δv=372, 2H), 4.59 (dd, J=8,12, 1H), 6.24 (bs, 1H), 6.8–7.2 (m, 3H).

$^{13}$C-NMR (δ, CDCl$_3$): 21.0, 26.0, 26.1, 26.25, 28.7, 32.2, 32.5, 40.2, 42.5, 47.5, 49.8, 51.5, 55.8, 125.2, 128.2, 131.2, 132.9, 138.7, 141.2, 167.6, 168.7.

IR (KBr, cm.$^{-1}$): 1682, 1658 (C=O).

MS (%): 449/451 (70/65, parent for Br$^{79}$/Br$^{81}$), 376/378 (100/95).

Anal. Calc'd. for C$_{23}$H$_{33}$BrN$_2$O$_2$: C. 61.47, H 7.40, N 6.23. Found: C 61.33, H 7.56, N 5.82.

HRMS: Calc'd. for $C^{23}H_{33}BrN_2O_2$: 448.1725. Found: 448.17405.

More polar isomer (trans):

$^1$H-NMR (δ, CDCl$_3$): 0.6–1.9 (m, 11H), 1.33 (s, 9H), 2.05 (m, 1H), 2.31 (s, 3H), 2.62 (m, 2H), 4.26 (AB$_q$, J$_{AB}$=14, Δν=23, 2H), 4.2 (m, 1H), 6.24 (bs, 1H), 7.0–7.2 (m, 3H).

$^{13}$C-NMR (δ, CDCl$_3$): 21.0, 26.0, 26.3, 26.4, 28.7, 30.3, 32.0, 37.7, 43.5, 45.5, 48.2, 51.4, 54.9, 124.2, 125.9, 128.4, 133.1, 137.7, 141.8, 167.2, 168.7.

IR (KBr, cm.$^{-1}$): 1660 (C=O).

MS (%): 449/451 (72/68, parent for Br$^{79}$/Br$^{81}$), 376/378 (100/95).

Anal. Calc'd. for $C_{23}H_{33}BrN_2O_2$: C 61.47, H 7.40, N 6.23. Found: C 61.44, H 7.38, N 5.93.

G. N-tert-Butyl 2-[3-azido-2-oxo-5-cyclohexyl-8-methyl-2,3,4,5-tetrahydro-1H-(1)benzazepin-1-yl]ethanoic acid amide To a 125 mL round-bottomed flask equipped with nitrogen inlet were added 3.11 grams (6.93 mmol) N-t-butyl 2-[3-bromo-2-oxo-5-cyclohexyl-8-methyl-2,3,4,5-tetrahydro-1H-(1)benzazepin-1-yl]ethanoic acid amide (more polar, trans, isomer), 0.54 grams (8.31 mmol) sodium azide, and 17 mL dry dimethylformamide. The reaction was heated at 80° C. for 6 hours (prolonged heating causes isomerization to the undesired trans isomer), cooled, and partitioned between ethyl acetate and water. The aqueous layer was extracted with more ethyl acetate, and the combined organic layer washed with water four times, brine once, dried over sodium sulfate, and evaporated. The residue was chromatographed on silica gel using hexane/ethyl acetate as eluant to afford the product as a white solid, M.P. 166°–169° C., 2.065 grams (72.5%).

$^1$H-NMR (δ, CDCl$_3$): 0.4–2.0 (m, 12H), 1.36 (s, 9H), 2.22 (m, 1H), 2.30 (s, 3H), 2.40 (m, 2H), 3.88 (dd, J=6,12, 1H), 4.05 (AB$_q$, J$_{AB}$=14, Δν=384, 2H), 6.31 (bs, 1H), 6.8–6.9 (m, 2H), 7.24 (s, 1H).

$^{13}$C-NMR (δ, CDCl$_3$): 21.0, 26.0, 26.1, 26.2, 28.7, 32.2, 32.5, 36.6, 40.3, 47.2, 51.5, 55.1, 58.5, 125.1, 128.1, 131.1, 133.2, 138.7, 140.5, 167.7, 171.0.

IR (KBr, cm.$^{-1}$): 2110 (N$_3$), 1678, 1658 (C=O).

FAB Mass Spectroscopy (%): 412 (parent+1, 83), 386 (67), 339 (100), 144 (76).

Anal. Calc'd. for $C_{23}H_{33}N_5O_2$: C 67.13, H 8.08, N 17.02. Found: C 66.87, H 7.82, N 16.75.

H. N-tert-Butyl 2-[3-amino-2-oxo-5-cyclohexyl-8-methyl-2,3,4,5-tetrahydro-1H-(1)benzazepin-1-yl]ethanoic acid amide N-tert-Butyl 2-[3-azido-2-oxo-5-cyclohexyl-8-methyl-2,3,4,5-tetrahydro-1H-(1)benzazepin-1-yl]ethanoic acid amide, 2.065 grams (5.02 mmol), was dissolved in 50 mL ethanol and treated with 413 mg 10% palladium-on-carbon at 45 psi hydrogen for 3 days. The catalyst was filtered and the reaction concentrated to a white foam, M.P. 177°–180° C., 1.86 grams (96%).

$^1$H-NMR (δ, CDCl$_3$): 0.4–2.0 (m, 13H), 1.36 (s, 9H), 2.28 (s, 3H), 2.3–2.5 (m, 2H), 3.47 (dd, J=7,12, 1H), 4.03 (AB$_q$, J$_{AB}$=15, Δν=378, 2H), 6.23 (bs, 1H), 6.87 (m, 2H), 7.24 (s, 1H).

$^{13}$C-NMR (δ, CDCl$_3$): 21.0, 26.1, 26.2, 26.3, 28.7, 32.3, 32.6, 40.3, 41.1, 47.9, 50.9, 51.4, 54.9, 124.8, 127.6, 131.0, 134.2, 138.1, 141.0, 168.1, 176.2.

IR (KBr, cm.$^{-1}$): 1666 (C=O).

FAB Mass Spectroscopy (%): 387 (parent+2, 100), 313 (97).

HRMS: Calc'd. for $C_{23}H_{35}N_3O_2$: 385.2721. Found: 385.27157.

I. N-tert-Butyl 2-[3-((3-tetrazolylphenyl)ureido)-2-oxo-5-cyclohexyl-8-methyl-2,3,4,5-tetrahydro-1H-(1)-benzaxepin-1-yl]ethanoic acid amide To a 100 mL round-bottomed flask equipped with condenser and nitrogen inlet were added 740 mg (1.71 mmol) 3-(N-triphenylmethyl)tetrazolylbenzoic acid, 514 mg (1.87 mmol) diphenylphosphoryl azide, 189 mg (1.87 mmol) triethylamine, and 10 mL dry benzene. Heating and addition of 2 mL dry tetrahydrofuran gave a solution, which was refluxed 3 hours, cooled, and 600 mg (1.56 mmol) N-tert-butyl 2-[3-amino-2-oxo-5-cyclohexyl-8-methyl-2,3,4,5-tetrahydro-1H-(1) benzazepin-1-yl]ethanoic acid amide was added. The reaction was refluxed for 15 hours, cooled, and chromatographed on silica gel using ethyl acetate/methylene chloride as eluant to afford the product as a white foam, 388 mg (31%). The foam was heated to reflux in methanol for 1.5 hours, cooled, evaporated, and triturated with methylene chloride/isopropyl ether to give a white solid, M.P. 220°–230° C., 184 mg (68%).

13C-NMR (δ, CDCl$_3$): 21.1, 22.8, 26.3, 26.4, 28.7, 32.4, 32.5, 32.6, 40.2, 40.3, 47.7, 52.2, 54.1, 68.4, 121.7, 123.9, 126.9, 127.7, 128.3, 128.4, 128.7, 129.4, 131.6, 133.6, 138.9, 140.3, 154.9, 167.4, 167.5.

FAB Mass Spectroscopy (%): 573 (24, parent+1), 500 (37), 313 (38), 243 (100), 197 (73), 132 (85).

Anal. Calc'd. for $C_{31}H_{40}N_8O_3 \cdot \frac{1}{2}H_2O$: C 64.01, H 7.10, N 19.26. Found: C 64.07, H 7.10, N 19.48.

EXAMPLE 10

A. 8-Methyl-1-naphthol

Prepared from the known (J. Chem. Soc., C, (1966) 523) 8-hydroxymethyl-1-naphthol by hydrogenolysis using 0.1 equiv. of 20 % palladium hydroxide on carbon (Pearlmann's catalyst) in ethanol at 45 psi hydrogen for 4 hours in quantitative yield, M.P. 56°–59° C.

B.  4-Phenyl-7-methyl-1,2,3,4-tetrahydronaphth-1-one and 4-phenyl-8-methyl-1,2,3,4-tetrahydronaphth-1-one Prepared from 8-methyl-1-naphthol using the procedure described above in Example 30 from Koptyug, V. A. and Andreeva, T. P., Zh. Organich. Khim., 7, 2398–2403 (1971) The products were separated by chromatography on silica gel using hexane/ethyl acetate as eluant and crystallized separately from methanol. X-ray analysis of single crystals of both compounds, grown in methanol, established the structures of the two isomers. 7-Methyl isomer, M.P. 72°–74° C.

$^1$H-NMR (δ, CDCl$_3$): 2.2–2.8 (m, 4H), 2.36 (s, 3H), 4.25 (m, 1H), 6.8–7.4 and 7.90 (m, 8H).

$^{13}$C-NMR (δ, CDCl$_3$): 21.0, 32.0, 36.8, 45.0, 126.7, 126.9, 127.2, 128.4, 128.6, 129.5, 132.6, 134.6, 143.5, 143.9, 198.4.

IR (cm.$^{-1}$, KBr): 1681 (C=O)

MS (%): 236 (parent, 100), 194 (70), 165 (50).

Anal. Calc'd. for $C_{17}H_{16}O$: C 86.40, H 6.82. Found: C 86.39, H 6.76.

8-Methyl isomer, M.P. 60°–63° C.

$^1$H-NMR (δ, CDCl$_3$): 2.2–2.7 (m, 4H), 2.68 (s, 3H), 4.28 (m, 1H), 6.8–7.3 (m, 8H).

$^{13}$C-NMR (δ, CDCl$_3$): 23.4, 31.2, 38.1, 46.1, 126.6, 126.8, 127.8, 128.6, 131.0, 131.6, 132.4, 141.2, 144.1, 147.3, 200.0.

IR (cm.$^{-1}$, KBr ): 1680 (C=O )

MS (%): 236 (parent, 100), 208 (85), 165 (50).

Anal. Calc'd. for $C_{17}H_{16}O$: C 86.40, H 6.82. Found: C 86.77, H 6.66.

The remainder of the synthesis was carried out as described in Example 9, using 4-phenyl-7-methyl-1,2,3,4-tetrahydronaphth-1-one:

C. 4-Phenyl-7-methyl-1,2,3,4-tetrahydronaphth-1-one oxime mp 143°–146° C., yield 72%.

Anal. Calc'd. for $C_{17}H_{17}NO$: C 81.24, H 6.82, N 5.57. Found: C 81.11, H 7.02, N 5.51.

D. 5-phenyl-8-methyl-2,3,4,5-tetrahydro-1H-(1)benzazepin-2-one mp 230°–234° C., yield 28.5%.

Anal. Calc'd. for $C_{17}H_{17}NO$: C 81.24, H 6.82, N 5.57. Found: C 81.25, H 6.89, N 5.54.

E. 3-Bromo-5-phenyl-8-methyl-2,3,4,5-tetrahydro-1H-(1)benzazepin-2-one mp 228°–232° C., 46% yield.

Anal. Calc'd. for $C_{17}H_{16}NO \cdot \frac{1}{4}H_2$: C 61.00, H 4.97, N 4.18. Found: C 61.07, H 5.01, N 4.38.

F. N-t-Butyl 2-[3-bromo-2-oxo-5-phenyl-8-methyl-2,3,4,5,-tetrahydro-1H-(1)benzazepin-1-yl]ethanoic acid amide M.P. 227°–230° C., 36% yield.

HRMS: Calc'd. for $C^{23}H_{27}N_2O_2Br$: 442.1249. Found: 442.12321.

G. N-tert-Butyl 2-[3-azido-2-oxo-5-phenyl-8-methyl-2,3,4,5-tetrahydro-1H-(1)benzazepin-1-yl]ethanoic acid amide 112°–115° C., 56% yield of the cis diastereomer isolated by chromatography on silica gel.

Anal. Calc'd. for $C_{23}H_{27}N_5O_2$: C 68.13, H 6.71, N 17.27. Found: C 68.40, H 6.82, N 17.12.

H. N-tert-Butyl 2-[3-amino-2-oxo-5-phenyl-8-methyl-2,3,4,5-tetrahydro-1H-(1)benzazepin-1-yl ethanoic acid amide M.P. 170°–180° C., 75% yield.

HRMS: Calc'd. for $C_{23}H_{29}N_3O_2$: 379.2253. Found: 379.2267.

I. N-tert-Butyl 2-[3-(3-carbomethoxylphenyl)ureido-2-oxo-5-phenyl-8-methyl-2,3,4,5-tetrahydro-1H-(1)benzazepin-1-yl]ethanoic acid amide To a 100 mL round-bottomed flask equipped with condenser and nitrogen inlet were added 475 mg (2.64 mmol) 3-carbomethoxybenzoic acid, 293 mg (2.90 mmol) triethylamine, 18 mL dry benzene, and 798 mg (2.90 mmol) diphenylphosphoryl azide. The reaction was refluxed 1 hour, cooled, and 1.00 grams (2.64 mmol) N-tert-butyl 2-[3-amino-2-oxo-5-phenyl-8-methyl-2,3,4,5-tetrahydro-1H-(1)benzazepin-1-yl]ethanoic acid amide added. The reaction was refluxed 14 hours, cooled, evaporated, and chromatographed on silica gel using ethyl acetate/methylene chloride as eluant to afford the product as a white foam, 951 mg (65%).

$^1$H-NMR (δ, CDCl$_3$): 0.6–2.0 (m, 12H), 1.12 (t, J=7, 3H), 1.20 (t, J=7, 3H), 2.24 (m, 1H), 2.32 (m, 1H), 2.95 (dd, J=4,10, 1H), 3.98 (m, 2H), 4.15 (m, 2H), 6.9–7.2 (m, 5H).

$^{13}$C-NMR (δ, CDCl$_3$): 13.9, 14.1, 26.4, 26.5, 31.1, 31.2, 32.0, 43.3, 49.7, 50.3, 61.0, 61.2, 126.3, 128.2, 128.5, 142.6, 169.4, 169.6.

IR (cm $^{-1}$, KBr): 1738 (C=O)

MS (%): 346 (parent, 12), 160 (100), 114 (60), 28 (59).

HRMS Calc'd. for $C_{21}H_{30}O_4$: 346.2136. Found: 346.21838.

J. N-tert-Butyl 2-[3-(3-carboxyphenyl)ureido-2-oxo-5-phenyl-8-methyl-2,3,4,5-tetrahydro-1H-(1)benzazepin-1-yl]ethanoic acid amide To a 100mL round-bottomed flask equipped with nitrogen inlet were added 920 mg (1.65 mmol) N-tert-butyl 2-[3-(3-carbomethoxyphenyl)ureido-2-oxo-5-phenyl-8-methyl-2,3,4,5-tetrahydro-1H-(1)benzazepin-1-yl]ethanoic acid amide and 16 mL tetrahydrofuran. To the stirring solution was added a solution of 347 mg (8.27 mmol) lithium hydroxide in 8 mL water, then 8 mL methanol was added to afford a solution, which was stirred at room temperature for 18 hours. The reaction was poured into 0.5N hydrochloric acid and the precipitate filtered, washed with water, and dried to white solid, M.P. 270°–273° C., 797 mg (89%).

$^1$H-NMR (δ, CDCl$_3$): 0.6–2.0 (m, 12H), 1.12 (t, J=7, 3H), 1.20 (t, J=7, 3H), 2.24 (m, 1H), 2.32 (m, 1H), 2.95 (dd, J=4,10, 1H), 3.98 (m, 2H), 4.15 (m, 2H), 6.9–7.2 (m, 5H).

$^{13}$C-NMR (δ, CDCl$_3$): 13.9, 14.1, 26.4, 26.5, 31.1, 31.2, 32.0, 43.3, 49.7, 50.3, 61.0, 61.2, 126.3, 128.2, 128.5, 142.6, 169.4, 169.6.

IR (cm.$^{-1}$, KBr): 1738 (C=O)

MS (%): 346 (parent, 12), 160 (100), 114 (60), 28 (59).

HRMS Calc'd. for $C_{21}H_{30}O_4$: 346.2136. Found: 346.21838.

K. N-tert-Butyl 2-[3-(3-(N-benzenesulfonyl)carboxamidophenyl)ureido-2-oxo-5-phenyl-8-methyl-2,3,4,5-tetrahydro-1H-(1)benzazepin-1-yl]ethanoic acid amide To a 100 mL round-bottomed flask equipped with nitrogen inlet were added 100 mg (0,184 mmol) N-tert-butyl 2-[3-(3-carboxyphenyl)ureido- 2-oxo-5-phenyl-8-methyl-2,3,4,5-tetrahydro-1H-(1)benzazepin-1-yl]ethanoic acid amide, 32 mg (0.203 mmol) benzenesulfonamide, 39 mg (0.203 mmol) 1-ethyl-3-(3-dimethylaminopropyl)carbodiimide, 25 mg (0.203 mmol) 4-dimethylaminopyridine, and 6 mL methylene chloride. The reaction was stirred at room temperature for 16 hours, poured into water, and extracted into ethyl acetate. The organic phase was washed with water, dilute hydrochloric acid, water, and brine, dried over sodium sulfate, and evaporated. The residue was chromatographed on silica gel using methanol/methylene chloride as eluant to afford the product as a glassy solid, which was triturated with methylene chloride/isopropyl ether to afford M.P. 190°–210° C., 23 mg (20 %).

$^1$H-NMR (δ, CDCl$_3$): 1.09 (s, 9H), 2.34 (s, 3H), 2.92 (m, 2H), 3.31 (AB$_q$, J$_{AB}$=16, Δv=124, 2H), 4.28 (m, 1H), 4.82 (m, 1H), 5.42 (m, 1H), 6.6–7.8 (m, 15H), 8.10 (d, J=8, 1H).

$^{13}$C-NMR (δ, CDCl$_3$): 21.0, 28.6, 29.7, 37.5, 43.9, 49.7, 51.9, 53.4, 118.7, 122.4, 123.6, 125.7, 126.2, 126.6, 128.3, 128.4, 128.5, 128.7, 128.8, 130.5, 131.4, 133.2, 135.1, 138.7, 139.6, 139.9, 140.8, 142.1, 155.6, 165.4, 166.8, 174.7.

IR (cm.$^{-1}$, KBr): 1643, 1679 (C=O)

MS (%): 682 (parent+1, 17), 609 (43), 307 (45), 251 (47), 234 (87), 208 (100), 91 (43).

Anal. Calc'd. for $C_{37}H_{39}N_5O_6S \cdot \frac{1}{2}H_2$: C 64.33, H 5.84, N 10.14. Found: C 64.36, H 5.86, N 10.09.

EXAMPLE 1

N-tert-Butyl 2-[3-(3-(N-methanesulfonyl)carboxamidophenyl)ureido-2-oxo-5-phenyl-8-methyl-2,3,4,5-tetrahydro-1H-(1)benzazepin-1-yl]ethanoic acid amide Prepared as in Example 10K using methanesulfonamide in 20 % yield, M.P. 190°–210° C.

HRMS Calc'd. for $C_{32}H_{37}N_5O_5SNa$: 642.2355. Found: 42.24129.

EXAMPLE 12

N-tert-Butyl 2-[3-(3-(N-trifluoromethanesulfonyl)carboxamidophenyl)ureido-2-oxo-5-phenyl-8-methyl-2,3,4,5-tetrahydro-1H-(1)benzazepin-1-yl]ethanoic acid amide Prepared as in Example 10K using trifluoromethanesulfonamide in 96% yield, M.P. 262°–272° C.

Anal. Calc'd. for $C_{32}H_{34}N_5O_6SF_3 \cdot \frac{5}{4}H_2O \cdot \frac{1}{2}H_2CO_3$: C 53.68, H 5.20, N 9.63. Found: C 53.70, H 5.09, N 9.56.

EXAMPLE 13

N-tert-Butyl 2-[3-(3-(N-(2-tolyl)sulfonyl)carboxamidophenyl)ureido-2-oxo-5-phenyl-8-methyl-2,3,4,5-tetrahydro-1H-(1)benzazepin-1-yl]ethanoic acid amide Prepared as in Example 10K using (2-tolyl)sulfonamide in 89.5% yield, M.P. solid 165°–175° C.

Anal. Calc'd. for $C_{38}H_{41}N_5O_6S \cdot \frac{5}{4}H_2O$: C 63.54, H 6.10, N 9.75. Found: C 63.74, H 6.14, N 9.50.

EXAMPLE 14

N-tert-Butyl 2-[3-(3-(N-ethanesulfonyl)carboxamidophenyl)ureido-2-oxo-5-phenyl-8-methyl-2,3,4,5-tetrahydro-1H-(1)benzazepin-1-yl]ethanoic acid amide Prepared as in Example 10K using ethanesulfonamide in 20.5% yield, M.P. 180°–190° C.

Anal. Calc'd. for $C_{33}H_{39}N_5O_6S \cdot H_2O$: C 60.81, H 6.34, N 10.74. Found: C 61.06, H 6.31, N 10.16.

EXAMPLE 15

N-tert-Butyl 2-[3-(3-(N-benzylsulfonyl)carboxamidophenyl)ureido-2-oxo-5-phenyl-8-methyl-2,3,4,5-tetrahydro-1H-(1)benzazepin-1-yl]ethanoic acid amide Prepared as in Example 10K using benzylsulfonamide in 74% yield, M.P. 160°–170° C.

Anal. Calc'd. for $C_{38}H_{41}N_5O_6S \cdot \frac{2}{3}H_2O$: C 64.48, H 6.03, N 9.89. Found: C 64.50, H 6.05, N 9.73.

EXAMPLE 16

N-tert-Butyl 2-[3-(3-tetrazolylphenyl)ureido-2-oxo-5-phenyl-8-methyl-2,3,4,5-tetrahydro-1H-(1)benzazepin-1-yl] ethanoic acid amide To a 100 mL round-bottomed flask equipped with condenser and nitrogen inlet were added 135 mg (0.686 mmol) 3-tetrazolylaniline hydrochloride (prepared as described in EP 514 133 A1), 0.12 mL (1.2 mmol) triethylamine, 67 mg (0.277 mmol) triphosgene, and 13 mL dry tetrahydrofuran at 0° C. Another 0.22 mL triethylamine was added, and the reaction was stirred at room temperature for 30 minutes. To the stirring reaction was added a solution of 200 mg (0.527 mmol) N-tert-butyl 2-(3-amino-2-oxo-5-phenyl-8-methyl-2,3,4,5-tetrahydro-1H-(1)benzazepin-1-yl) ethanoic acid amide in 2 mL dry tetrahydrofuran. The reaction was stirred at room temperature for 3 hours, diluted with ethyl acetate and 20% aqueous acetic acid, and the layeres separated, and the organic layer washed with water and brine, dried over sodium sulfate, and evaporated. The residue was chromatographed on silica gel using methanol/ethyl acetate as eluant to afford 81 mg (27%) of a white solid, M.P. 228°–238° C.

13C-NMR ($\delta$, CDCl$_3$): 21.8, 29.3, 38.4, 45.2, 51.1, 54.3, 63.5, 118.3, 122.0, 122.1, 126.5, 127.5, 127.6, 129.5, 130.8, 131.9, 136.7, 140.3, 143.4, 157.0, 164.5, 169.9.

IR (cm.$^{-1}$, KBr): 1645 (C=O).

FAB Mass Spectroscopy (%): 567 (68, parent+1), 589 (32, parent+Na$^+$), 494 (100), 307 (54), 208 (60).

HRMS Calc'd. for $C_{31}H_{35}N_8O_3$: 567.2832. Found: 567.28364.

EXAMPLE 17

N-tert-Butyl 2-[3-(3-(N-(5-tetrazolyl))carboxamidophenyl)ureido-2-oxo-5-phenyl-8-methyl-2,3,4,5-tetrahydro-1H-(1)benzazepin-1-yl]ethanoic acid amide Prepared as in Example 10K using 5-aminotetrazole in 75% yield, M.P. 225°–235° C.

Anal. Calc'd. for $C_{32}H_{35}N_9O_4$: C 63.04, H 5.79, N 20.68. Found: C 62.78, H 6.14, N 19.84.

EXAMPLE 18

N-tert-Butyl 2-[3-((3-tetrazolyphenyl)ureido)-2-oxo-5-benzyl-8-methyl-2,3,4,5-tetrahydro-1H-(1)benzazepin-1-yl] ethanoic acid amide A. 3-Benzyl-3-(4-tolyl)butanoic acid Prepared as in Example 9 as a yellow oil, which was used directly in the next step.

B. 4-Benzyl-7-methyl-1,2,3,4-tetrahydronaphth-1-one

Prepared as in Example 9 as a yellow oil, and converted directly to the oxime.

C. 4-Benzyl-7-methyl-1,2,3,4-tetrahydronaphth-1-one oxime

Prepared as in Example 9 in 60% yield as a light yellow solid.

HRMS: Calc'd. for $C_{17}H_{23}NO$: 257.1776. Found: 257.17903.

D. 5-Benzyl-8-methyl-2,3,4,5-tetrahydro-1H(1)benzazepin-2-one

Prepared as in Example 9 in 79% yield, M.P. 143°–145° C.

Anal. Calc'd. for $C_{18}H_{19}NO$: C 81.47, H 7.22, N 5.28. Found: C 81.22, H 7.33, N 4.95.

E. 3-Bromo-5-benzyl-8-methyl-2,3,4,5-tetrahydro-1H-(1)benzazepin-2-one

Prepared as in Example 9 in 82% yield, M.P. 197°–200° C.

Anal. Calc'd. for $C_{18}H_{18}BrNO \cdot \frac{1}{4}H_2$: C 61.99, H 5.35, N 4.01. Found: C 61.96, H 5.32, N 3.81.

F. N-t-Butyl 2-[3-bromo-2-oxo-5-benzyl-8-methyl-2,3,4,5,-tetrahydro-1H-(1)benzazepin-1-yl]ethanoic acid amide Prepared as in Example 9, with crystallization of the crude reaction product from methylene chloride/isopropyl ether to give the more polar isomer, M.P. 167°–170° C., in 52% yield.

Anal. Calc'd. for $C_{24}H_{29}BrN_2O_2 \cdot \frac{1}{4}H_2$: C 62.41, H 6.44, N 6.06. Found: C 62.32, H 6.51, N 6.12.

G. N-tert-Butyl 2-[3-azido-2-oxo-5-benzyl-8-methyl-2,3,4,5-tetrahydro-1H-(1)benzazepin-1-yl]ethanoic acid amide Prepared as in Example 9 in 70% yield as a solid, M.P. 169°–172° C.

Anal. Calc'd. for $C_{24}H_{29}N_5O_2 \cdot \frac{1}{4}H_2$: C 67.98, H 7.01, N 16.52. Found: C 68.12, H 6.97, N 16.35.

H. N-tert-Butyl 2-[3-amino-2-oxo-5-benzyl-8-methyl-2,3,4,5-tetrahydro-1H-(1)benzazepin-1-yl]ethanoic acid amide Prepared as in Example 9, M.P. 155°–165° C., in approximately 100% yield.

HRMS: Calc'd. for $C_{24}H_{31}N_3O_2$: 393.2409. Found: 393.24427.

I. N-tert-Butyl 2-[3-((3-tetrazolylphenyl)ureido)-2-oxo-5-benzyl-8-methyl-2,3,4,5-tetrahydro-1H-(1)benzazepin-1-yl] ethanoic acid amide Prepared as in Example 9 as a white solid, M.P. 230°–235° C., in 50% yield.

$^{13}$C-NMR (δ, CDCl$_3$): 20.5, 28.1, 38.9, 41.1, 43.0, 49.9, 51.5, 53.7, 116.7, 120.6, 120.7, 124.1, 125.1, 125.5, 126.1, 127.8, 128.1, 128.3, 128.8, 129.5, 130.8, 133.3, 138.4, 139.3, 140.0, 140.4, 155.3, 168.0, 173.5.

FAB Mass Spectroscopy (%): 603 (50, parent+Na$^+$), 508 (30), 321 (33), 248 (36), 144 (52), 91 (100).

Anal. Calc'd. for C$_{32}$H$_{36}$N$_8$O$_3$·½H$_2$O: C 65.18, H 6.32, N 19.00. Found: C 65.12, H 6.40, N 18.81.

EXAMPLE 19

N-tert-Butyl 2-[3-((3-tetrazolylphenyl)ureido)-2-oxo-5-isopropyl-8-methyl-2,3, 4,5-tetrahydro-1H-(1)benzazepin-1-yl]ethanoic acid amide A. 3-Isopropyl-3-(4-tolyl)butanoic acid Prepared as in Example 9 as an oil, which was used directly in the next step.

HRMS Calc'd. for C$_{21}$H$_{30}$O$_4$: 346.2136. Found: 346.21838.

B. 4-Isopropyl-7-methyl-1,2,3,4-tetrahydronaphth-1-one

Prepared as in Example 9 as an oil in 18% yield for both steps.

HRMS: Calc'd. for C$_{18}$H$_{18}$O: 202.1353. Found: 202.13701.

Preparation of 5-isopropyl-8-methyl-2,3,4,5-tetrahydro-1H-(1)benzazepin-2-one

C. 4-Isopropyl-7-methyl-1,2,3,4-tetrahydronaphth-1-one oxime

Prepared as in Example 9 in 100% yield, M.P. 90°–92° C.

Anal. Calc'd. for C$_{14}$H$_{19}$NO: C. 77.38, H 8.81, N 6.44. Found: C 77.44, H 8.83, N 6.69.

D. 5-Isopropyl-8-methyl-1,2,3,4,5-tetrahydro-1H-(1)benzazepin-2-one

Prepared as in Example 9 in 56% yield, M.P. 141.5°–143.5° C.

Anal. Calc'd. for C$_{14}$H$_{19}$NO·⅛H$_2$O: C 76.59, H 8.84, N 6.38. Found: C 76.94, H 8.97, N 6.17.

E. 3-Bromo-5-isopropyl-8-methyl-2,3,4,5-tetrahydro-1H-(1)benzazepin-2-one

Prepared as in Example 9 in 85% yield, M.P. 138°–143° C.

Anal. Calc'd. for C$_{14}$H$_{18}$BrNO: C 56.77, H 6.12, N 4.73. Found: C 56.73, H 6.36, N 4.52.

F. N-t-Butyl 2-[3-bromo-2-oxo-5-isopropyl-8-methyl-2,3,4,5,-tetrahydro-1H-(1)benzazepin-1-yl]ethanoic acid amide Prepared as in Example 9, with chromatographic separation of the diastereomers n silica gel using hexane/ethyl acetate as eluant, giving the less polar isomer, M.P. 176°–179° C., in 35% yield, and the more polar isomer, M.P. 161°–164° C., 51% yield.

Less polar isomer:

Anal. Calc'd. for C$_{20}$H$_{29}$BrN$_2$O$_2$: C 58.68, H 7.14, N 6.84. Found: C 58.77, H 7.33, N 6.74.

More polar isomer:

Anal. Calc'd. for C$_{20}$H$_{29}$BrN$_2$O$_2$·¼H$_2$O: C 58.04, H 7.18, N 6.77. Found: C 58.05, H 7.24, N 6.73.

G. N-tert-Butyl 2-[3-azido-2-oxo-5-isopropyl-8-methyl-2,3,4,5-tetrahydro-1H-(1)benzazepin-1yl]ethanoic acid amide Prepared as in Example 9 in 74.5% yield, 157°–159° C.

Anal. Calc'd. for C$_{20}$H$_{29}$N$_5$O$_2$·¼H$_2$O: C 63.89, H 7.91, N 18.63. Found: C 63.99, H 7.74, N 18.45.

H. N-tert-Butyl 2-[3-amino-2-oxo-5-isopropyl-8methyl-2,3,4,5-tetrahydro-1H-(1)benzazepin-1-yl]ethanoic acid amide Prepared as in Example 9 in 100% yield as a foam, M.P. 100°–120° C.

HRMS: Calc'd. for C$_{20}$H$_{31}$N$_3$O$_2$: 345.2416. Found: 345.23982.

I. N-tert-Butyl 2-[3-((3-tetrazolylphenyl)ureido)-2-oxo-5-isopropyl-8-methyl-23,4,5-tetrahydro-1H-(1)benzazepin-1-yl]ethanoic acid amide Prepared as in Example 9 in 59% yield, M.P. 235°–240° C.

$^{13}$C-NMR (δ, CDCl$_3$): 20.9, 21.0, 21.8, 28.4, 28.5, 29.5, 29.6, 30.2, 30.8, 30.9, 37.4, 38.1, 50.4, 51.7, 53.9, 54.1, 116.9, 121.0, 121.2, 124.1, 124.3, 125.2, 125.4, 128.1, 128.2, 129.5, 129.6, 129.7, 130.5, 131.5, 131.6, 133.9, 134.0, 138.5, 138.6, 140.0, 140.1, 140.2, 155.2, 155.8, 166.3, 167.7, 167.8, 172.8, 174.1.

FAB Mass Spectroscopy (%): 555 (28, parent+Na$^+$), 445 (40), 273 (50), 200 (66), 174 (65), 132 (100).

Anal. Calc'd. for C$_{28}$H$_{36}$N$_8$O$_3$·¼CO$_2$: C 62.41, H 6.67, N 20.61. Found: C 62.55, H 6.90, N 20.35.

EXAMPLE 20

Preparation of N-tert-Butyl 2-[3-(3-tetrazolylphenyl)ureido-2-oxo-5-(4-tolyl)-8-methyl-2,3,4,5-tetrahydro-1H-(1) benzazepin-1-yl]ethanoic acid amide A. 4,4-Di(4-tolyl)-but-3-enoic acid To a 500 mL round-bottomed flask equipped with condenser and nitrogen inlet were added 29.7 grams (141 mmol) 4,4'-dimethylbenzophenone and 141 mL t-butanol forming a solution, followed by 17.4 grams (155 mmol) potassium t-butoxide and 29.5 grams (170 mmol) diethyl succinate. The reaction was refluxed for 18 hours, cooled, and acidified with 6N hydrochloric acid, then poured into water and extracted with ethyl acetate. The organic layer was dried over sodium sulfate and evaporated, and the residue taken up in 200 mL glacial acetic acid. It was then treated with 70 mL 48% hydrobromic acid and refluxed for 36 hours. The reaction was cooled, partitioned between water and ethyl acetate, and the combined organic layers washed with water and brine, dried over sodium sulfate, and evaporated. The residue was chromatographed on silica gel using methylene chloride/methanol as eluant to afford the product as low melting solid, 25.0 grams (66%), R$_f$=0.25 in 5% methanol/methylene chloride on silica gel. This material was used directly in the next step.

B. 4,4-Di(4-tolyl)-butanoic acid

The oil from the preceding step was hydrogenated in 150 mL ethyl acetate with 5 grams of 10% palladium on carbon under 25 psi hydrogen for 1.5 hours to afford, after chromatography on silica gel using methylene chloride/methanol as eluant, 19 grams (75%) of an oil.

HRMS: Calc'd. for C$_{18}$H$_{20}$O$_2$: 268.1458. Found: 268.14445.

C. 4-(4-Tolyl)-7-methyl-1,2,3,4-tetrahydronaphth-1-one

Prepared as in Example 9B to afford the product as a solid, M.P. 90°–92° C. in 49% yield.

Anal. Calc'd. for C$_{18}$H$_{20}$O: C 86.36, H 7.25. Found: C 86.32, H 7.27.

The remaining steps were carried out as in Example 9:

D. 4-(4-Tolyl)-7-methyl-1,2,3,4-tetrahydronaphth-1-one oxime mp 174°–177° C., yield 74%.

Anal. Calc'd. for $C_{18}H_{19}NO$: C 81.47, H 7.22, N 5.28. Found: C 81.45, H 7.19, N 5.11.

E. 5-4-Tolyl)-8-methyl-1,2,3,4,5-tetrahydro-1H-(1)benzazepin-2-one mp 218°–220° C., yield 73%.

Anal. Calc'd. for $C_{18}H_{19}NO$: C 81.47, H 7.22, N 5.28. Found: C 81.14, H 7.00, N 5.21.

F. 3-Bromo-5-(4-tolyl)-8-methyl-2,3,4,5-tetrahydro-1H-(1)benzazepin-2-one mp 195°–201° C., 87% yield.

Anal. Calc'd. for $C_{18}H_{18}NOBr,.\frac{1}{2}H_2O$: C 61.20, H 5.42, N 3.97. Found: C 61.48, H 5.13, N 3.92.

G. N-t-Butyl 2-[3-bromo-2-oxo-5-(4-tolyl)-8-methyl-2,3,4,5,-tetrahydro-1H-(1)benzazepin-1-yl]ethanoic acid amide mp 181°–183° C., 63% yield of the more polar isomer diastereomer.

Anal. Calc'd. for $C_{24}H_{29}N_2O_2Br$: C 63.02, H 6.39, N 6.12. Found: C 63.11, H 6.37, N 6.10.

H. N-tert-Butyl 2-[3-azido-2-oxo-5-(4-tolyl)-8-methyl-2,3,4,5-tetrahydro-1H-(1)benzazepin-1-yl]ethanoic acid amide

195°–196.5° C., 49%.

Anal. Calc'd. for $C_{24}H_{29}N_5O_2$: C 68.71, H 6.97, N 16.69. Found: C 68.82, H 6.93, N 16.67.

I. N-tert-Butyl 2-[3-amino-2-oxo-5-(4-tolyl)-8-methyl-2,3,4,5-tetrahydro-1H-(1)benzazepin-1yl]ethanoic acid amide mp 273°–276° C., 31% yield.

Anal. Calc'd. for $C_{24}H_{31}N_3O_2.H_2CO_3$: C 66.57, H 7.26, N 9.32. Found: C 66.39, H 7.46, N 9.61.

J. N-tert-Butyl 2-[3-(3-tetrazolylphenyl)ureido-2-oxo-5-(4-tolyl)-8-methyl-2,3,4,5-tetrahydro-1H-(1)benzazepin-1-yl]ethanoic acid amide mp 223°–230° C., 39% yield.

$^{13}$C-NMR ($\delta$, CDCl$_3$): 21.0, 21.2, 28.8, 43.5, 50.8, 51.9, 54.4, 119.2, 122.5, 124.8, 126.1, 128.8, 129.0, 129.6, 129.7, 130.8, 135.1, 136.3, 137.6, 139.4, 140.5, 140.6, 154.3, 155.1, 167.5, 175.7.

FAB Mass Spectroscopy (%): 581 (54, parent+1), 508 (100), 321 (42), 248 (60), 222 (98).

Anal. Calc'd. for $C_{32}H_{36}N_8O_3.\frac{1}{3}H_2$: C 65.51, H 6.30, N 9.10. Found: C 65.40, H 6.48, N 18.94.

EXAMPLE 21

Preparation of N-tert-Butyl 2-[3-(3-tetrazolylphenyl)ureido-2-oxo-5-phenyl-8-ethyl-2,3,4,5-tetrahydro-1H-(1)benzazepin-1-yl]ethanoic acid amide A. 3-(4-Ethyobenzoyl)-propionic acid To a 250 mL round-bottomed flask equipped with condenser and nitrogen inlet were added 20 grams (200 mmol) succinic anhydride, 53.2 grams (400 mmol) aluminum chloride, and 83 mL ethyl benzene. The reaction was heated at 85° C. for 12 hours, cooled, and quenched with water and acidified with 6N hydrochloric acid. The mixture was then extracted into ethyl acetate, and the organic layer dried over sodium sulfate and evaporated. The residue was washed with methylene chloride/hexane and finally hexane to afford a solid, 24.3 grams (59%), which was used directly in the next step.

B. 4-(4-Ethylphenyl)-butanoic acid

To a 500 mL round-bottomed flask equipped with condenser and nitrogen inlet were added 41.2 grams (200 mmol) 3-(4-ethylbenzoyl)-propionic acid, activated zinc prepared from 82.4 grams (400 mmol) mossy zinc and 8.2 grams mercuric chloride in 125 mL water and 8 mL concentrated hydrochloric acid, 77 mL water, 177 mL concentrated hydrochloric acid, and 100 mL toluene. The mixture was refluxed 60 hours with addition of two 50 mL portions of concentrated hydrochloric acid, cooled, and the layers separated. The organic layer was extracted into 3N aqueous sodium hydroxide, which was then acidified and extracted into ethyl acetate. The organic layer was dried over sodium sulfate and evaporated to afford 28.9 grams (75%), M.P. 70°–72° C.

Anal. Calc'd. for $C_{12}H_{16}O_2$: C 74.97, H 8.39. Found: C 75.00, H 8.23.

C. 7-Ethyl-1-tetralone

Prepared as in Example 9B to give 17.9 grams (68%) of an oil.

HRMS: Calc'd. for $C_{12}H_{14}O$: 174.1045. Found: 174.10316.

D. 7-Ethyl-1-acetoxynaphthalene

To a 250 mL round-bottomed flask equipped with condenser and nitrogen inlet were added 17.9 grams (103 mmol) 7-ethyl-1-tetralone, 1.96 grams (10 mmol) p-toluenesulfonic acid, and 125 mL isopropenyl acetate. The reaction was refluxed 18 hours, cooled, and 46.76 grams (206 mmol) 2,3-dicyano-5,6-dichlorobenzoquinone added. After the exotherm had subsided, the reaction was refluxed 2 hours and cooled. The resulting precipitate was filtered using ethyl acetate, and the filtrate washed with dilute aqueous sodium hydroxide, dilute hydrochloric acid, and water, then dried over sodium sulfate and evaporated. The residue was chromatographed on silica gel using hexane/ethyl acetate to afford an oil, 11.47 grams (52%). The oil was used directly in the next step.

MS (%): 214 (parent, 38), 172 (100), 157 (39), 43 (30).

IR (cm.$^{-1}$, KBr): 1767 (C=O)

The remaining steps follow Example 10:

E. 4-Phenyl-7-ethyl-1,2,3,4-tetrahydronaphth-1-one

Prepared as in Example 10B in 41% yield as an oil.

HRMS: Calc'd. for $C_{18}H_{18}O$: 250.1353. Found: 250.13337.

F. 4-Phenyl-7-ethyl-1,2,3,4-tetrahydronaphth-1-one oxime mp 120°–122° C., yield 100%.

Anal. Calc'd. for $C_{18}H_{19}NO$: C 81.47, H 7.22, N 5.28. Found: C 81.45, H 7.17, N 5.23.

G. 5-phenyl-8-ethyl-2,3,4,5-tetrahydro-1H-(1)benzazepin-2-one mp 190°–193° C., yield 66%.

Anal. Calc'd. for $C_{18}H_{19}NO$: C 81.47, H 7.22, N 5.28. Found: C 81.56, H 7.16, N 5.32.

H. 3-Bromo-5-phenyl-8-ethyl-2,3,4,5-tetrahydro-1H-(1)benzazepin-2-one mp 231°–235° C., 76% yield.

Anal. Calc'd. for $C_{18}H_{18}NOBr$: C 62.80, H 5.27, N 4.07. Found: C 62.45, H 5.11, N 3.95.

I. N-t-Butyl 2-[3-bromo-2-oxo-5-phenyl-8-ethyl-2,3,4,5,-tetrahydro-1H-(1)benzazepin-1-yl]ethanoic acid amide mp 211°–213° C., 66% yield.

Anal. Calc'd. for $C_{24}H_{29}N_2O_2Br$: C 63.02, H 6.39, N 6.12. Found: C 63.14, H 6.60, N 6.12.

J. N-tert-Butyl 2-[3-azido-2-oxo-5-phenyl-8-ethyl-2,3,4,5-tetrahydro-1H-(1) benzazepin-1-yl]ethanoic acid amide 124°–127° C., 73% yield of the cis isomer.

Anal. Calc'd. for $C_{24}H_{29}N_5O_2$: C 68.71, H 6.97, N 16.69. Found: C 68.75, H 6.72, N 16.59.

K. N-tert-Butyl 2-[3-amino-2-oxo-5-phenyl-8-ethyl-2,3,4,5-tetrahydro-1H-(1)benzazepin-1-yl]ethanoic acid amide mp 68°–78° C., 100% yield.

HRMS: Calc'd. for $C_{24}H_{31}N_3O_2$: 393.2409. Found: 393.24513.

L. N-tert-Butyl 2-[3-(3-tetrazolylphenyl)ureido-2-oxo-5-phenyl-8-ethyl-2,3,4,5-tetrahydro-1H-(1)benzazepin-1yl]ethanoic acid amide Prepared as in Example 9 in 58% yield, M.P. 250°–256° C.

Anal. Calc'd. for $C_{32}H_{36}N_8O_3 \cdot \frac{1}{2}H_2$: C 65.18, H 6.32, N 19.00. Found: C 65.19, H 6.51, N 18.85.

EXAMPLE 22

Preparation of N-tert-Butyl 2-[3-((3-tetrazolylphenyl)ureido)-2-oxo-5-(2-tolyl)-8-methyl-2,3,4,5-tetrahydro-1H-(1)benzazepin-1-yl]ethanoic acid amide, in analogy with Example 9.

A. 5-(4-Tolyl), 5-(2-tolyl)butyrolactone

Prepared as an oil as in Example 9 and used directly to prepare 3-cyclohexyl-3-(4-tolyl)butanoic acid, also an oil, which was used directly in the next step.

B. 4-(2-Tolyl)-7-methyl-1,2,3,4-tetrahydronaphth-1-one.

Prepared as in Example 9, using chromatography on silica gel with hexane/ethyl acetate to separate the desired isomer from the 5-(4-tolyl)-6-methyl tetralone isomer, yield overall to this point, as an oil.

HRMS: Calc'd. for $C_{18}H_{18}O$: 250.1353. Found: 250.13444.

C. 4-(2-Tolyl)-7-methyl-1,2,3,4-tetrahydronaphth-1-one oxime

Prepared as in Example 9 in % yield as a low-melting solid. p 279.

D. 5-(2-Tolyl)-8-methyl-2,3,4,5-tetrahydro-1H-(1)benzazepin-2-one

Prepared as in Example 9 in 30% yield, M.P. 215°–219° C.

Anal. Calc'd. for $C_{18}H_{19}NO \cdot \frac{1}{4}H_2O$: C 80.11, H 7.28, N 5.19. Found: C 80.25, H 7.36, N 5.09.

HRMS: Calc'd. for $C_{18}H_{19}NO$: 265.1462. Found: 265.14476.

E. 3-Bromo-5-(2-tolyl)-8-methyl-2,3,4,5-tetrahydro-1H-(1)benzazepin-2-one

Prepared as in Example 9 in 79% yield, M.P. 200°–205° C.

Anal. Calc'd. for $C_{18}H_{18}BrNO$: C 62.80, H 5.27, N 4.07. Found: C 62.948, H 5.19, N 3.72.

F. N-t-Butyl 2-[3-bromo-2-oxo-5-(2-tolyl)-8-methyl-2,3,4,5-tetrahydro-1H-(1)benzazepin-1-yl]ethanoic acid amide Prepared as in Example 9, using crystallization from methylene chloride/hexane to separate out the desired trans isomer, M.P. 219°–221° C., in 86% yield.

Anal. Calc'd. for $C_{24}H_{29}BrN_2O_2 \cdot \frac{1}{4}H_2O$: C 62.41, H 6.44, N 6.06. Found: C 62.34, H 6.50, N 5.96.

G. N-tert-Butyl 2-[3-azido-2-oxo-5-(2-tolyl)-8-methyl-2,3,4,5-tetrahydro-1H-(1)benzazepin-1-yl]ethanoic acid amide Prepared a in Example 9 in 88% yield, M.P. 137°–139° C.

Anal. Calc'd. for $C_{25}H_{29}N_5O_2$: C 68.71, H 6.97, N 16.69. Found: C 68.45, H 6.96, N 16.72.

HRMS: Calc'd. for $C_{25}H_{29}N_5O_2$: 419.2315. Found: 419.23307.

H. N-tert-Butyl 2-[3-amino-2-oxo-5-(2-tolyl)-8-methyl-2,3,4,5-tetrahydro-1H-(1)benzazepin-1yl]ethanoic acid amide Prepared as in Example 9 in 100% yield, as a solid, M.P. 70°–90° C.

HRMS: Calc'd. for $C_{24}H_{31}N_3O_2$: 393.2409. Found: 393.23797.

I. N-tert-Butyl 2-[3-((3-tetrazolylphenyl)ureido)-2-oxo-5-(2-tolyl)-8-methyl-2,3,4,5-tetrahydro-1H-(1)benzazepin-1-yl]ethanoic acid amide Prepared as in Example 9 as a white solid, M.P. 238°–243° C., in 48% yield.

$^{13}$C-NMR ($\delta$, $CDCl_3$): 21.0, 28.4, 29.3, 29.6, 34.1, 38.3, 42.7, 50.1, 50.8, 53.1, 53.7, 116.9, 121.1, 121.2, 123.4, 125.3, 125.4, 125.6, 125.8, 125.9, 126.6, 126.8, 127.1, 128.1, 128.4, 129.6, 129.7, 130.0, 130.9, 131.3, 133.3, 134.4, 137.4, 137.9, 155.5, 167.9, 170.7, 173.1.

FAB Mass Spectroscopy (%): 581 (7, parent+1), 508 (11), 309 (15), 155 (87), 137 (15), 121 (22), 119 (100), 103 (58).

Anal. Calc'd. for $C_{32}H_{36}N_8O_3 \cdot H_2$: C 64.2 0, H 6.40, N 18.72. Found: C 64.46, H 6.46, N 18.51.

EXAMPLE 23

Preparation of N-(1-Methylcylohexy) 2-[3-(3tetrazolylphenyl)ureido-2-oxo-5-phenyl-8-ethyl-2,3,4,5-tetrahydro-1H-(1)benzazepin-1-yl]ethanoic acid amide A. N-(1-Methylcyclohexyl)2-[3-bromo-2-oxo-5-phenyl-8-ethyl-2,3,4,5,-tetrahydro-1H-(1)benzazepin-1-yl]ethanoic acid amide Prepared as in Example 20I from 3-bromo-5-phenyl-8-ethyl-2,3,4,5-tetrahydro-1H-(1)benzazepin-2-one using N-(1-methylcyclohexyl)-iodoacetamide, M.P. 156°–158° C., 80% yield for the trans isomer.

Anal. Calc'd. for $C_{27}H_{33}N_2O_2Br$: C 65.19, H 6.69, N 5.63. Found: C 65.30, H 6.80, N 5.54.

B. N-(1-Methylcyclohexyl) 2-[3-azido-2-oxo-5-phenyl-8-ethyl-2,3,4,5-tetrahydro-1H-(1)benzazepin-1-yl]ethanoic acid amide Prepared as in Example 20 as a foam, 71% yield.

HRMS: Calc'd. for $C_{27}H_{33}N_5O_2$: 459.2627. Found: 459.26453.

C. N-(1-Methylcyclohexyl) 2-[3-amino-2-oxo-5-phenyl-8-ethyl-2,3,4,5-tetrahydro-1H-(1)benzazepin-1-yl]ethanoic acid amide Prepared as in Example 20, M.P. 85°–100° C., 100% yield.

HRMS: Calc'd. for $C_{27}H_{35}N_3O_2$: 433.2721. Found: 433.27089.

D. N-(1-Methylcyclohexyl) 2-[3-(3-tetrazolylphenyl)ureido-2-oxo-5phenyl-8-ethyl-2,3,4,5-tetrahydro-1H, (1)benzazepin-1-yl ]ethanoic acid amide Prepared as in Example 20 in 63.5% yield, M.P. 215°–220° C.

Anal. Calc'd. for $C_{35}H_{40}N_8O_3 \cdot \frac{2}{3}H_2O$: C 66.44, H 6.58, N 17.71. Found: C 66.42, H 6.62, N 17.67.

EXAMPLE 24

Preparation of N-(1-Methylcyclohexyl) 2-[3-(3-tetrazolylphenyl)ureido)-2-oxo-5-phenyl-8-methyl-2,3,4,5-tetrahydro-1H-(1)benzazepin-1-yl]ethanoic acid amide A. N-(1-Methylcyclohexyl)-2-[3-bromo-2-oxo-5-phenyl-8-methyl-2,3,4,5,-tetrahydro-1H-(1)benzazepin-1yl]ethanoic acid amide Prepared as in Example 20I from 3-bromo-5-phenyl-8-methyl-2,3,4,5-tetrahydro-1H-(1)benzazepin-2-one using N-(1-methylcyclohexyl)-iodoacetamide, M.P. x° C., x% yield for the trans isomer.

Anal. Calc'd. for $C_{27}H_{33}N_2Br$: C x, H 6.69, N 5.63. Found: C 65.30, H 6.80, N 5.54.

B. N-(1-Methylcyclohexyl)2-[3-azido-2-oxo-5-phenyl-8-methyl-2,3,4,5-tetrahydro-1H-(1)benzazepin-1-yl]ethanoic acid amide Prepared as in Example 20 as a foam, x% yield.

HRMS: Calc'd. for $C_{26}H_{31}N_5O_2$: x. Found: 459.26453.

C. N-(1-Methylcyclohexyl)2-[3-amino-2-oxo-5-phenyl-8-methyl-2,3,4,5-tetrahydro-1H-(1)benzazepin-1-yl]ethanoic acid amide Prepared as in Example 20, M.P. x° C., 100% yield.

HRMS: Calc'd. for $C_{26}H_{33}N_3O_2$: x. Found: 433.27089.

D. N-(1-Methylcyclohexyl) 2-[3-(3-tetrazolyphenyl)ureido)-2-oxo-5-phenyl-8-methyl-2,3,4,5-tetrahydro-1H-(1)benzazepin-1-yl]ethanoic acid amide Prepared as in Example 20 in 80% yield, M.P. 259°–263° C.

Anal. Calc'd. for $C_{34}H_{38}N_8O_3 \cdot \frac{1}{2}H_2O$: C 66.65, H 6.38, N 18.20. Found: C 66.63, H 6.35, N 18.24.

EXAMPLE 25

N-tert-Butyl 2-[3-((3-tetrazolylphenyl)ureido)-2-oxo-5-cyclohexylmethyl-8-methyl-2,3,4,5-tetrahydro-1H-(1)benzazepin-1-yl]ethanoic acid amide A. 3-Cyclohexylmethyl-3-(4-tolyl)butanoic acid Prepared as in Example 9 as a yellow oil, which was used directly in the next step.

B. 4-Cyclohexylmethyl-7-methyl -1,2,3,4-tetrahydronaphth-1-one

Prepared as in Example 9 as a yellow oil in 20 % overall yield, and converted directly to the oxime.

HRMS Calc'd. for $C_{18}H_{24}O$: 256.1827. Found: 256.18335.

C. 4-Cyclohexylmethyl-7-methyl-1,2,3,4-tetrahydronaphth-1-one oxime

Prepared as in Example 9 as a dark yellow oil which was converted directly to the lactam.

D. 5-Cyclohexylmethyl-8-methyl-2,3,4,5-tetrahydro-1H-(1)benzazepin-2-one

Prepared as in Example 9 in 72% overall yield, M.P. 155°–157° C.

Anal. Calc'd. for $C_{18}H_{25}NO$: C 79.66, H 9.28, N 5.16. Found: C 79.53, H 9.35, N 5.17.

E. 3-Bromo-5-cyclohexylmethyl-8-methyl-2,3,4,5-tetrahydro-1H-(1)benzazepin-2-one Prepared as in Example 9 in 92% yield, M.P. 150°–158° C.

Anal. Calc'd. for $C_{18}H_{24}BrNO$: C 61.72, H 6.91, N 4.00. Found: C 62.09, H 7.05, N 3.99.

F. N-t-Butyl 2- [3-bromo-2-oxo-5-cyclohexylmethyl-8-methyl-2,3,4,5-tetrahydro-1H-(1)benzazepin-1-yl]ethanoic acid amide Prepared as in Example 9. After chromatography on silica using hexane/ethyl acetate as eluant to separate diastereomers, the more polar trans diastereomer was crystallized from hexane to give M.P. 166°–170° C., in 49% yield.

Anal. Calc'd. for $C_{24}H_{35}BrN_2O_2 \cdot \frac{1}{4}H_2O$: C 61.60, H 7.65, N 5.99. Found: C 61.60, H 7.94, N 5.95.

G. N-tert-Butyl 2-[3-azido-2-oxo-5-cyclohexylmethyl-8-methyl-2,3,4,5-tetrahydro-1H-(1)benzazepin-1-yl]ethanoic acid amide Prepared as in Example 9 in 61% yield as a solid, M.P. 100°–105° C.

Anal. Calc'd. for $C_{24}H_{35}N_5O_2 \cdot \frac{1}{4}H_2O$: C 67.03, H 8.32, N 16.28. Found: C 67.31, H 8.68, N 16.55.

H. N-tert-Butyl 2-[3-amino-2-oxo-5-cyclohexylmethyl-8-methyl-2,3,4,5-tetrahydro-1H-(1)benzazepin-1-yl]ethanoic acid amide Prepared as in Example 9, M.P. 239°–247° C., in quantitative yield.

Anal. Calc'd. for $C_{24}H_{37}N_3O_2 \cdot 3H_2O$: C 673.55, H 9.55, N 9.26. Found: C 63.95, H 9.21, N 9.31.

I. N-tert-Butyl 2-[3-((3-tetrazolylphenyl)ureido)-2-oxo-5-cyclohexylmethyl-8-methyl-2,3,4,5-tetrahydro-1H-(1)benzazepin-1yl]ethanoic acid amide Prepared as in Example 9 as a white solid, M.P. 240°–245° C., in 69% yield.

$^{13}$C-NMR ($\delta$, CDCl$_3$): 21.1, 26.1, 26.3, 26.5, 28.8, 32.8, 34.1, 36.0, 38.6, 39.2, 43.3, 51.3, 52.2, 53.4, 54.3, 115.7, 119.6, 122.5, 124.1, 128.5, 129.5, 131.1, 138.9, 140.4, 154.5, 155.0, 167.4, 176.5, 177.3.

MS (%): 587 (16, parent+1), 514 (38), 327 (48), 158 (46), 155 (36), 146 (57), 144 (51), 132 (48), 120 (43), 119 (100), 103 (45).

Anal. Calc'd. for $C_{32}H_{42}N_8O_3 \cdot \frac{1}{3}H_2$: C 64.84, H 7.26, N 18.90. Found: C 64.74, H 7.45, N 18.88.

EXAMPLE 26

Preparation of N-tert-Butyl 2-[3-(3-(N-(5-tetrazolyl))carboxyamidophenyl)ureido-2-oxo-5-cyclohexyl-8-methyl-2,3,4,5-tetrahydro-1H-(1)benzazepin-1-yl]ethanoic acid amide A. N-tert-Butyl 2-[3-(3-carbomethoxyphenyl)ureido-2-oxo-5-cyclohexyl-8-methyl-2,3,4,5-tetrahydro-1H-(1)]benzazepin-1-yl]ethanoic acid amide Prepared as in Example 10I, using N-tert-butyl 2-[3-amino-2-oxo-5-cyclohexyl-8-methyl-2,3,4,5-tetrahydro-1H-(1)benzazepin-1-yl]ethanoic acid amide (Example 9H), in 69% yield, as a white solid, M.P. 130°–140° C.

Anal. Calc'd. for $C_{32}H_{42}N_4O_5 \cdot \frac{1}{2}H_2$: C. 67.23, H 7.58, N 9.80. Found: C 67.36, H 8.07, N 9.63.

B. N-tert-Butyl 2-[3-(3-carboxyphenyl)ureido-2-oxo-5-cyclohexyl-8-methyl-2,3,4,5-tetrahydro-1H-(1)benzazepin-1yl]ethanoic acid amide Prepared as in Example 10J as a white solid, M.P. 240°250° C., in 90% yield.

$^{13}$C-NMR ($\delta$, CDCl$_3$): 20.7, 25.8, 26.1, 28.2, 32.1, 32.4, 37.7, 40.7, 47.1, 50.6, 53.1, 54.3, 122.9, 124.1, 126.6, 127.1, 129.2, 129.5, 129.8, 131.8, 133.4, 137.4, 139.1, 139.3, 156.45, 169.0, 171.0, 174.9.

Anal. Calc'd. for $C_{31}H_{40}N_4O_5$: C 67.86, H 7.35, N 10.21. Found: C 67.96, H 7.65, N 10.09.

C. N-tert-Butyl 2-[3-(3-carboxyphenyl)ureido-2-oxo-5-cyclohexyl-8-methyl-2,3,4,5-tetrahydro-1H-(1)benzazepin-1-yl]ethanoic acid amide potassium salt Prepared from the carboxylic acid in the preceding step using potassium hydroxide in methanol, M.P. 228°–238° C., in 90% yield.

Anal Calc'd. for $C_{31}H_{39}N_4O_5K \cdot H_2$: C 61.57, H 6.83, N 9.26. Found: C 61.33, H 7.17, N 9.09.

D. N-tert-Butyl 2-[3-(3-(N-(5-tetrazolyl))carboxamidophenyl)ureido-2-oxo-5-cyclohexyl-8-methyl-2,3,4,5-tetrahydro-1H-(1)benzazepin-1-yl]ethanoic acid amide Prepared as in Example 10K using 5-aminotetrazole as a white solid M.P. 228°–235° C., from isopropyl ether in 50% yield.

$^{13}$C-NMR (δ, CDCl$_3$): 21.0, 22.8, 22.9, 26.2, 26.3, 28.9, 32.3, 32.4, 37.8, 37.9, 40.4, 47.8, 50.0, 52.1, 53.9, 68.3, 117.9, 122.1, 122.2, 123.3, 124.6, 128.4, 128.9, 130.9, 131.2, 133.3, 139.3, 139.5, 140.4, 150.9, 155.3, 166.9, 167.5, 175.9.

FAB Mass Spectroscopy (%): 616 (60, parent+1), 313 (65), 144 (82), 132 (100), 120 (65).

Anal. Calc'd. for $C_{32}H_{41}N_9O_4 \cdot \frac{1}{4}H_2O \cdot \frac{1}{4}(C_6H_{14}O)$: C. 62.70, H 7.07, N 19.67. Found: C 62.37, H 7.18, N 19.94.

EXAMPLE 27

N-tert-Butyl 2-[3-(3-N-methanesulfonyl)carboxamidophenyl)ureido-2-oxo-5-cyclohexyl-8-methyl-2,3,4,5-tetrahydro-1H-(1)benzazepin-1yl]ethanoic acid amide Prepared as in Example 10K using methanesulfonamide as a white solid from isopropyl ether in 28% yield, M.P. 198°–208° C.

$^{13}$C-NMR (δ, CDCl$_3$): 20.9, 22.7, 26.1, 26.3, 28.6, 32.3, 32.5, 37.8, 40.4, 41.3, 47.6, 50.0, 51.8, 51.9, 53.8, 68.5, 118.2, 122.5, 123.4, 124.4, 128.2, 129.0, 131.3, 131.8, 133.5, 138.8, 138.9, 140.4, 155.2, 166.8, 166.9, 167.0, 174.9.

FAB Mass Spectroscopy (%): 648 (70, parent+Na$^+$), 553 (75), 313 (72), 144 (82), 132 (100).

Anal. Calc'd. for $C_{32}H_{43}N_5O_6S$: C. 61.42, H 6.93, N 11.19. Found: C 61.42, H 7.24, N 11.11.

EXAMPLE 28

N-tert-Butyl 2-[3-(3-(N-trifluoromethanesulfonyl)carboxamidophenyl)ureido-2-oxo-5-cyclohexyl-8-methyl-2,3,4,5-tetrahydro-1H-(1)benzazepin-1-yl]ethanoic acid amide Prepared as in Example 10K using trifluoromethanesulfonamide in 78% yield, M.P. 275°–285° C.

$^{13}$C-NMR (δ, CDCl$_3$): 20.9, 22.7, 26.0, 26.1, 28.4, 32.2, 32.4, 40.3, 47.4, 52.0, 53.3, 68.5, 123.8, 127.9, 128.2, 131.4, 133.5, 135.9, 138.4, 140.1, 140.2, 155.4, 168.0, 173.9.

FAB Mass Spectroscopy (%): 718 (100, parent+K$^+$), 662 (14), 394 (12), 144 (26), 132 (25).

Anal. Calc'd. for $C_{32}H_{40}N_5O_6SF_3 \cdot \frac{5}{4}H_2$: C 54.73, H 6.10, N 9.97. Found: C 54.74, H 5.72, N 9.58.

EXAMPLE 29

Preparation of (+) and (−) N-tert-Butyl 2-(3-(3-tetrazolylphenylureido)-2-oxo-5-phenyl-8-methyl-2,3,4,5-tetrahydro-1H-(1) benzazepin-1-yl) ethanoic acid amide N-tert-Butyl 2-(3-(L-2-(t-butoxycarbonylamino)-3phenylpropionamido)-2-oxo-5-phenyl-8-methyl-2,3,4,5-tetrahydro-1H-(1)benzazepin-1yl]ethanoic acid amide To a 125 mL round-bottomed flask equipped with nitrogen inlet were added 1.00 grams (2.64 mmol) N-tert-butyl 2-(3-amino-2-oxo-5-phenyl-8-methyl-2,3,4,5-(1)benzazepin-1-yl) ethanoic acid amide, 0.70 grams (2.64 mmol) t-BOC-L-phenylalanine, 0.404 grams (2.64 mmol) N-hydroxybenzotriazole, 0.506 grams (2.64 mmol) ethyl (dimethylamino-propyl) carbodiimide hydrochloride, and 0. 662 mL (4.75 mmol) triethylamine. The reaction was stirred at room temperature for 14 hours (tlc R$_f$=0.35/0.32 for the diastereomers in 1/1 ethyl acetate/hexane), taken up in ethyl acetate, washed with water, 1N hydrochloric acid, water, aqueous saturated sodium bicarbonate solution, water, and brine, dried over sodium sulfate, and evaporated to a foam, suitable for further use, 1.60 grams (97%).

$^1$H-NMR (δ, CDCl$_3$): 1.26, 1.31 (s's, 9H), 1.373, 1.379 (s's, 9H), 2.30, 2.34 (s's, 3H), 2.8–3.1 (m, 5H), 3.03 (AB$_q$, J$_{AB}$=15, Δv=275) and 3.19 (AB$_q$, J$_{AB}$=16, Δv=294) 2H, 3.4–3.5 (m, 2H), 5.1, 5.4, and 5.9 (m's, NH, 3H), 6.7–7.4 (m, 13H).

FAB Mass Spectroscopy (%): 627 (parent+1, 19), 527 (100), 498 (61), 454 (76), 234 (77), 208 (82), 120 (64).

N-tert-Butyl 2-(3-(L-2-amino-3-phenylpropionamido)-2-oxo-5-phenyl-8-methyl-2,3,4,5--tetrahydro-1H-(1)benzazepin-1-yl) ethanoic acid amide To a 125 mL round-bottomed flask equipped with nitrogen inlet were added the above foam and 40 mL ethyl acetate. The solution was cooled to 0° C. and saturated with hydrochloric acid gas, then stirred at 0° C. allowing to warm to room temperature over 2.5 hours (tlc indicates no starting material, products at R$_f$=0.3 and 0.2 in 5% aqueous acetonitrile), then poured into a large flask containing aqueous bicarbonate solution. The organic layer was washed with further bicarbonate, brine, dried over sodium sulfate, and evaporated. The residue was chromatographed on silica gel using 3% aqueous acetonitrile as eluant to afford each diastereomer as an oil/foam.

Less polar diastereomer, 618 mg (46%), a$_D$=−71.8 (c=1, CH$_2$Cl$_2$):

$^1$H-NMR (δ, CDCl$_3$): 1.27 (s, 9H), 1.40 (broad s, 2H), 2.30 (s, 3H), 2.52 (m, 1H), 2.68 (dd, J=9,16, 1H), 2.92 (m, 1H), 3.05 (AB$_q$, J$_{AB}$=16, Dn=302, 2H) (3.11 (dd, J=3.5,12, 1H), 3.53 (m, 1H), 4.10 (m, 1H), 4.52 (m, 1H), 5.99 (s, 1H), 6.9–7.4 (m, 13H), 8.11 (d, J=7, 1H).

$^{13}$C-NMR (δ, CDCl$_3$): 21.1, 28.6, 36.6, 40.9, 43.8, 48.9, 51.2, 53.8, 56.2, 125.8, 126.3, 126.8, 128.2, 128.4, 128.6, 129.4, 130.4, 135.1, 137.7, 138.9, 140.9, 142.0, 167.9, 171.1, 173.7.

More polar diastereomer, 590 mg (44%), a$_D$=+46.3 (C=1, CH$_2$Cl$_2$):

$^1$H-NMR (δ, CDCl$_3$): 1.24 (s, 9H), 1.40 (broad s, 2H), 2.26 (s, 3H), 258 (m, 2H), 2.93 (m, 1H), 3.07 (AB$_q$, J$_{AB}$=16, Δv=299, 2H) (3.17 (dd, J=4,13, 1H), 3.55 (m, 1H), 4.13 (m, 1H), 4.53 (m, 1H), 5.99 (s, 1H), 6.9–7.4 (m, 13H), 7.89 (d, J=7, 1H).

$^{13}$C-NMR (δ, CDCl$_3$): 21.1, 28.6, 36.3, 41.1, 43.8, 49.0, 51.3, 53.9, 56.7, 125.7, 126.3, 126.7, 128.3, 128.4, 128.7, 129.3, 130.4, 135.1, 138.1, 139.0 140.9, 141.9, 167.9, 171.1, 174.0.

N-tert-Butyl 2-(3-amino-2-oxo-5phenyl-8-methyl-2,3,4,5-tetrahydro-1H-(1)benzazepin-1yl)ethanoic acid amide, (−) diastereomer To a 100 mL round-bottomed flask equipped with condenser nitrogen inlet were added 618 mg (1.17 mmol) of the less polar diastereomer of N-tert-butyl 2-(3-(L-2-amino-3-phenylpropionamido)-2-oxo-5-phenyl-8-methyl-2,3,4,5-tetrahydro-1H-(1)benzazepin-1-yl)ethanoic acid amide, 10 mL 1,2-dichloroethane, and 0.148 mL (1.23 mmol) phenylisothiocyanate. The solution was refluxed for 1.2 hours, cooled, and evaporated. The residue (major product R$_f$=0.3 in 1/1 ethyl acetate/hexane) was taken up in 10 mL trifluoroacetic acid and heated at 60° C. for 50 minutes (tlc, R$_f$=0.3 for product in 10% methanol in methylene chloride), cooled, and evaporated. The residue was taken up in ethyl acetate, washed with aqueous sodium bicarbonate solution, then extracted into 2×50 mL 1N hydrochloric acid. The acid layer was washed with ethyl acetate, the pH adjusted to 8 with sodium carbonate, and extracted into ethyl acetate. The organic layer was washed with brine, dried over sodium sulfate, and evaporated to a foam, suitable for further use, 282 mg (64%), $a_D$=−131.4 (c=1, C$_2$Cl$_2$). Spectral data matched that of the racemate.

N-tert-Butyl 2-(3-amino-2oxo-5phenyl-8-methyl-2,3,4,5-tetrahydro-1H-(1)benzazepin-1-yl]ethanoic acid amide, (+) diastereomer Prepared as above in 63% yield, $a_D$=+138.0 (c=1, CH$_2$Cl$_2$).

N-tert-Butyl 2-(3-(3-tetrazolylphenylureido)-2-oxo-5-phenyl-8-methyl-2,3,4,5-tetrahydro-1H-(1)benzazepin-1-yl) ethanoic acid amide (−) diastereomer Prepared from N-tert-butyl 2-(3-amino-2-oxo-5-phenyl-8-methyl-2,3,4,5-tetrahydro-1H-(1)benzazepin-1-yl) ethanoic acid amide, (+) diastereomer, as in Example 9I in 34% yield, M.P. 194°–204° C. from methylene chloride/isopropyl ether, $a_D$=−101.4 (c=1, CH$_2$Cl$_2$). Spectral data matched those of the racemate given in Example 16.

EXAMPLE 30

Preparation of cis,cis-N-tert-butyl-2-[3-((3-(N-methanesulfonyl)carboxamidophenyl)ureido)-2-oxo-5(2-methoxyphenyl)7-phenyl-2,3,4,5,6,7-hexahydroazepin-1-yl]ethanoic acid amide A. 4-(2-Methoxyphenyl)-4-hydroxycyclohexanone ethylene ketal Prepared in analogy with Example 1 in 90% yield as an oil and used directly in the next step.

$^1$H-NMR (δ, CDCl$_3$): 1.7–1.9 (m, 2H), 2.0–2.3 (m, 6H), 3.78 and 3.88 (s's, 3H), 3.9–4.1 (m, 4H), 6.9–7.4 (m, 4H). MS (%): 264 (1, parent), 165 (10), 135 (40), 101 (100).

B. 4-(2-Methoxyphenyl)cyclohexanone

Prepared in analogy with Example 1 in 44% yield as a low-melting solid. $^1$H-NMR (δ, CDCl$_3$): 1.91 (m, 2H), 2.22 (m, 2H), 2.52 (m, 4H), 3.46 (triplet of triplets, J=4,12, 1H), 3.84 (s, 3H), 6.8–7.3 (m, 4H).

MS (%): 204 (100, parent), 147 (80), 134 (50), 119 (45), 91 (40).

C. 2-Chloro-4-(2-methoxyphenyl)cyclohexanone

Prepared in analogy with Example 1 and yellow oil in 100% yield as a mixture of diastereomers which was used directly in the next step.

$^1$H-NMR (δ, CDCl$_3$): 1.8–2.7 (m, 6H), 3.40 and 3.55 (m's for each diastereomer, 1H), 3.70 and 3.83 (s's for each diasteromer, 3H), 4.65 and 5.31 (m's, 1H), 6.8–7.2 (m, 4H).

MS (%): 238/240 (100/30, Cl$^{35}$/Cl$^{37}$, parent), 147 (50), 121 (40), 91 (40).

D. 2-Phenyl-4-(2-methoxyphenyl)cyclohexanone

Prepared in analogy with Example 1 as an oil in 25.5% yield. The oil, which is only the cis diastereomer, was used directly in the next step.

$^1$H-NMR (δ, CDCl$_3$): 1.8–2.7 (m, 6H), 3.6–3.8 (m, 2H), 3.83, 3.85 (s's, 3H), 6.8–7.3 (m, 9H).

MS (%): 280 (100, parent), 134 (80), 121 (65), 91 (50).

E. 2-Phenyl-4-(2-methoxyphenyl)cyclohexanone oxime

Prepared in analogy with Example 1 in 66% yield as a yellow solid.

$^1$H-NMR (δ, CDCl$_3$): 1.6–2.2 (m, 4H), 3.35 (m, 1H), 3.55 (m, 2H), 3.80 (m, 2H), 3.81 (s, 3H), 6.8–7.4 (m, 9H).

$^{13}$C-NMR (δ, CDCl$_3$): 24.8, 31.3, 36.4, 40.2, 49.5, 55.3, 110.4, 120.7, 126.3, 126.9, 127.2, 128.3, 128.7, 133.0, 140.0, 156.5, 162.5.

MS (%): 296 (parent+1, 100), 155 (70), 135 (60), 119 (100), 103 (72).

HRMS: Calc'd. for C$_{19}$H$_{21}$NO$_2$: 295.1572. Found: 295.1605.

F. 5-(2-Methoxyphenyl)-7-phenyl-2,3,4,5,6,7-hexahydroazepin-2-one

Prepared in analogy with Example 1 in 33% yield as a white solid.

$^1$H-NMR (δ, CDCl$_3$): 1.8–2.2 (m, 4H), 2.6–2.8 (m, 2H), 3.38 (m, 1H), 3.79 (s, 3H), 4.59 (m, 1H), 5.76 (bs, 1H), N H), 6.8–7.4 (9H).

$^{13}$C-NMR (δ, CDCl$_3$): 29.0, 36.5, 40.8, 43.5, 55.3, 58.4, 110.5, 120.7, 126.3, 126.7, 127.4, 128.3, 129.2, 134.1, 142.2, 156.0, 177.0.

MS (%): 296 (100, parent), 192 (18), 147 (19).

HRMS Calc'd. for C$_{19}$H$_{21}$NO$_2$: 295.1572. Found: 295.1545.

G. 3-Bromo-5-(2-metboxyphenyl)-7-phenyl-2,3,4,5,6,7-hexahydroazepin-2-one

Prepared in analogy with Example 1 as a foam in 29% yield, as a mixture of diastereomers.

$^1$H-NMR (δ, CDCl$_3$): 2.0–2.2 (m, 2H), 2.3–2.6 (m, 2H), 3.53 (m, 1H), 3.79 and 3.81 (s's for the diastereomers, 3H), 4.54 and 4.77 (m's for diastereomers, 1H), 4.99 (m, 1H), 6.6–7.4 (m, 10H).

H. N-(t-Butyl)-2-oxo-3-bromo-5-(2-methoxyphenyl)-7-phenyl-hexahydroazepin-1-yl]ethanoic amide Prepared in analogy with Example 1 in 79% yield as a foam, a mixture of diastereomers.

$^1$H-NMR (δ, CDCl$_3$): 1.27 (s, 9H), 2.2–2.6 (m, 4H), 3.57 (m, 1H), 3.59 (AB$_q$, J$_{AB}$15, Δν=167, 2H), 3.765 (s, 3H),4.98 (d, J=10, 1H), 5.28 (m, 1H), 5.70 (bs, 1H, NH), 6.71 (m, 1H), 7.2–7.4 (m, 9H).

$^{13}$C-NMR (δ, CDCl$_3$): 26.6, 28.3, 28.7, 38.8, 51.3, 55.6, 62.3, 112.3, 128.0, 128.4, 129.0, 129.4, 130.2, 130.4, 167.7, 170.5.

IR (cm.$^{-1}$, KBr): 1664 (C=O)

MS (%): 487 (parent, 40), 414 (45), 119 (53), 91 (100).

I. N-(t-Butyl)-2-oxo-3-azido-5-(2-methoxyphenyl)-7-phenyl-hexahydroazepin-1-yl ethanoic amide Prepared in analogy with Example 1 and separated into a less polar isomer (33% yield) and a more polar isomer, the desired cis product, in 44.5% yield as a foam.

$^1$H-NMR (δ, CDCl$_3$): 1.28 (s, 9H), 2.1–2.3 (m, 3H), 2.55 (m, 1H), 3.54 (m, 1H), 3.60 (AB$_q$, J$_{AB}$=15, Δν=173, 2H), 3.78 (s, 3H), 4.53 (m, 1H), 4.91 (m, 1H), 5.65 (bs, 1H), 6.73 (m, 1H), 7.3–7.5 (m, 9H).

$^{13}$C-NMR (δ, CDCl$_3$): 28.7, 36.0, 37.2, 38.0, 48.4, 51.1, 55.6, 61.1, 61.5, 112.3, 113.2, 128.7, 129.0, 129.4, 130.1, 130.5, 134.7, 137.9, 155.2, 167.7, 172.5.

IR (KBr, cm.$^{-1}$): 2104 (N$_3$), 1661 (C=O).

HRMS: Calc'd. for C$_{25}$H$_{31}$N$_5$O$_3$: 449.2427. Found: 449.2430.

J. N-(t-Butyl)-2-oxo-3-amino-5-(2-methoxyphenyl)-7-phenyl-hexahydroazepin-1-yl ethanoic amide Prepared in analogy with Example 1 in 79% yield as a foam.

$^1$H-NMR (δ, CDCl$_3$): 1.24 (singlet, 9H), 2.3–2.7 (multipiers, 4H), 3.71 (s, 3H), 3.8–4.1 (m, 4H), 5.2 (m, 1H), 6.7–7.5 (m, 10H), 8.3 (m, 2H).

IR (cm.$^{-1}$, KBr): 1664 (C=O)

MS (%): 424 (parent+1, 100), 351 (55), 266 (48), 223 (80).

HRMS Calc'd. for C$_{25}$H$_{33}$N$_3$O$_3$: 423.2514. Found: 423.2611.

K. cis,cis-N-tert-Butyl-2-[3((3-carbomethoxyphenyl)ureido)-2-oxo-5-(2-methoxyphenyl-7-phenyl-2,3,4,5,6,7-hexahydroazepin-1-yl]ethanoic acid amide Prepared as in Example 1K and afford a white solid in 63% yield, which was used directly in the next step, M.P. 230°–232° C.

¹H-NMR (δ, CDCl₃): 1.15 (s, 9H), 1.9–2.4 (m, 4H), 3.4 (m, 1H), 3.58 (AB$_q$, J$_{AB}$=16, Δv=106), 3.71 (S, 3H), 3.81 (s, 3H), 3.80 (s, 3H), 5.16 (m, 2H), 5.75 (bs, 1H), 6.7–7.7 (m, 15H), 7.95 (bs, 1H).

FAB Mass Spectroscopy (%): 6015 (parent+1, 11), 528 (44), 223 (100).

L. cis,cis-N-tert-Butyl-2-[3-((3-carboxyphenyl)ureido)-2-oxo-5-(2-methoxyphenyl)-7-phenyl-2,3,4,5,6,7-hexahydroazepin-1-yl]ethanoic acid amide Prepared as in Example 1L in quantitative yield as a white solid.

¹H-NMR (δ, CDCl₃): 1.16 (s, 9H), 1.9–2.4 (m, 4H), 3.0–3.5 (m, 4H), 3.70 (s, 3H), 5.18 (m, 1H), 5.67 (m, 1H), 6.6–7.9 and 8.28 (m, 16H).

FAB Mass Spectroscopy (%): 587 (parent+1, 13), 514 (20), 223 (100).

Anal. Calc'd. for C₃₃H₃₈N₄O₆.½H₂: C 66.54, H 6.60, N 9.41. Found: C 66.29, H 6.73, N 9.26.

M. cis,cis-N-tert-Butyl-2-[3-(3-(N-methanesulfonyl)carboxamido-phenyl)ureido)-2-oxo-5-(2)-7-phenyl-2,3,4,5,6,7-hexahydroazepin-1-yl]ethanoic acid amide Prepared as in Example 1M 81% yield.

Anal. Calc'd. for C₃₄H₄₁N₅O₇S.H₂: C 59.90, H 6.36, N 10.27. Found: C 59.87, H 6.34, N 10.31.

EXAMPLE 31 cis,cis-N-tert-Butyl-2-[3-((3-tetrazolylphenyl)ureido)-2-oxo-5-(2-methoxyphenyl)-7-phenyl-2,3,4,5,6,7-hexahydroazepin-1-yl]ethanoic acid amide Prepared as in Example 9 in 33% yield as a solid, M.P. 205° C. (dec.).

¹H-NMR (δ, CDCl₃): 1.12 (s, 9H), 1.9–2.4 (m, 4H), 3.5 (m, 2H), 3.60 (AB$_q$, J$_{AB}$=16, Δv=91), 3.70 (s, 3H), 5.1 (m, 1H), 5.78 (bs, 1H), 6.6–7.6 (m, 15H), 7.85 (bs, 1H, NH).

¹³C-NMR (δ, CDCl₃): 28.3, 37.6, 37.9, 38.1, 47.9, 51.0, 52.3, 61.3, 110.5, 116.9, 120.7, 121.0, 121.3, 127.0, 127.5, 128.6, 128.8, 129.4, 129.9, 133.0, 138.2, 155.0, 168.0, 175.0.

FAB Mass Spectroscopy (%): 611 (parent+1, 3), 538 (16), 223 (46), 91 (100).

Anal. Calc'd. for C₃₃H₃₈N₈O₄H₂: C 63.04, H 6.41, N 17.82. Found: C 63.24, H 6.32, N 17.82.

EXAMPLE 32

Preparation of (+) and (−) N-tert-butyl 2-[3-(3-carboxyphenyl)ureido-2-oxo-5-cyclohexyl-8-methyl-2,3,4,5-tetrahydro-1H-(1)benzazepin,1-yl]ethanoic acid amide N-tert-Butyl-2-(3-(L-2t-butoxycarbonylamino)-3-phenylpropionamido)-2-oxo-5-cyclohexyl-8-methyl-2,3,4,5-tetrahydro-1H-(1)benzazepin-1-yl) ethanoic acid amide Prepared as in Example 29 as a foam, which was used directly in the next step.

N-tert-Butyl 2-(3-(L-2amino-3-phenylpropionamido)-2-oxo-5-cyclohexyl-8-methyl-2,3,4,5-tetrahydro-1H(1)benzazepin-1-yl) ethanoic acid amide Prepared as in Example 29 and separated by column chromatography using 3–5% aqueous acetonitrile to afford two diastereomers.

Less polar diastereomer, 41%, M.P. 85°–95° C.:

HRMS Calc'd for C₃₂H₄₄N₄O₃: 532.3403. Found: 532.34533.

More polar diastereomer, 40%, M.P. 90°–95° C.:

HRMS Calc'd for C₃₂H₄₄N₄O₃: 532.3403. Found: 532.34314.

N-tert-Butyl 2-(3-amino-2-oxo-5-cyclohexyl-8-methyl-2,3,4,5-tetrahydro-1H-(1)benzazepin-1-yl) ethanoic acid amide, (−) diastereomer Prepared as in Example 29 as a solid, M.P. 83°–103° C., in 48% yield, a$_D$=−57.2 (c=1, CH₂Cl₂). Spectral data matched that of the racemate.

N-tert-Butyl 2-(3-amino-2-oxo-5-cyclohexyl-8-methyl-2,3,4,5-tetrahydro-1H-(1)benzazepin-1-yl) ethanoic acid amide, (+) diastereomer Prepared as above, M.P. 90°–100° C., in 86% yield, a$_D$=+60.0 (c=1, CH₂Cl₂).

N-tert-Butyl 2-[3-(3-t-butoxycarbonylphenyl)ureido-2-oxo-5-cyclohexyl-8-methyl-2,3,4,5-tetrahydro-1H-(1)benzazepin-1-yl]ethanoic acid amide, (−)-diastereomer Prepared as in Example 10I, using 3-t-butoxycarbonylbenzoic acid, in 72% yield as a white solid, M.P. 145°–155° C., a$_D$=−71.2 (c=1, CH₂Cl₂).

FAB Mass Spectroscopy (%): 605 (parent+1, 9), 571 (92), 532 (27), 476 (33), 311 (43), 257 (62), 144 (100).

N-tert-Butyl 2-[3-(3-carboxyphenyl)ureido-2-oxo-5-cyclohexyl-8-methyl-2,3,4,5-tetrahydro-1H-(1)benzazepin-1-yl]ethanoic acid amide, (−)-diastereomer Prepared as in Example 10J as a white solid, M.P. 150°–160° C., in 50% yield, a$_D$=−78.9 (c=1, MeOH). Spectral data matched that of the racemate.

N-tert-Butyl 2-[3-(3-t-butoxycarbonylphenyl)ureido-2-oxo-5-cyclohexyl-8-methyl-2,3,4,5-tetrahydro-1H-(1)benzazepin-1yl]ethanoic acid amide, (+)-diasteromer Prepared as in Example 10I, using 3-t-butoxycarbonylbenzoic acid, in 77% yield as a white solid, M.P. 145°–155° C., a$_D$=+73.7 (c=1, CH₂Cl₂).

¹H-NMR (δ, CDCl₃): 0.4–1.0 (m, 4H), 1.2–1.6 (m, 6H), 1.36 (s, 9H), 1.52 (s, 9H), 1.9–2.1 (m, 2H), 2.29 (s, 3H), 2.43 (m, 1H), 2.66 (m, 1H), 4.21 (AB$_q$, J$_{AB}$=16, Δv=389, 2H), 4.61 (m, 1H), 6.23 (m, 1H, NH), 6.6–8.0 (m, 5H).

¹³C-NMR (δ, CDCl₃): 21.0, 25.8, 25.9, 26.2, 28.1, 28.8, 32.2, 38.1, 40.4, 47.6, 50.5, 53.9, 81.0, 119.7, 123.2, 123.4, 124.2, 128.0, 1128.7, 131.4, 132.1, 133.6, 138.3, 139.6, 140.7, 155.0, 166.0, 167.3, 174.1.

N-tert-Butyl 2-[3-(3-carboxyphenyl)ureido-2-oxo-5-cyclohexyl-8-methyl-2,3,4,5-tetrahydro-1H-(1)benzazepin-1-yl]ethanoic acid amide, (+)-diastereomer Prepared as in Example 10J as a white solid, M.P. 170°–180° C., in 99% yield, a$_D$=+82.1 (c=1, MeOH). Spectral data matched that of the racemate.

¹³C-NMR (δ, CDCl₃): 21.0, 26.1, 26.3, 28.6, 32.2, 32.5, 38.7, 40.8, 47.5, 50.2, 52.0, 54.5, 119.851, 123.0, 123.1, 124.4, 124.5, 124.6, 128.4, 129.2, 129.4, 131.5, 133.6, 138.5, 140.1, 140.2, 154.8, 167.2, 170.2, 174.6.

N-tert-Butyl 2-[3-(3-carboxyphenyl)ureido-2-oxo-5-cyclohexyl-8-methyl-1,2,3,4,5-tetrahydro-1H-(1)benzazepin-1-yl]ethanoic acid amide potassium salt, (+)-diastereomer Prepared from the carboxylic acid in the preceding step using potassium hydroxide in methanol, M.P. 210–230° C., in 100% yield, a$_D$=+×(c=1, MeOH).

EXAMPLE 33

N-(1-t-butyl)-2-[3-((3-carbomethoxy)phenyl)ureido)-2-oxo-5-(phenyl)-8-methyl-2,3,4,5tetrahydro-1H-(1)benzazepin-1-yl]ethanoic acid amide To a 100 ml round bottomed flask equipped with condenser and a nitrogen inlet were added 143 mg (0.792 mmol) 3-carbomethoxybenzoic acid, 0.188 mL (0.872 mmol)

diphenylphosphorylazide, 0.121 mL (0.872 mmol) triethylamine, and 5 mL dry benzene. The reaction was heated to reflux for 1 hour, cooled, 300 mg (0.792 mmol) N-(1-t-butyl)-2-[3-amino-2-oxo-5-(phenyl)-8-methyl-2,3,4,5-tetrahydro-1H-(1)benzazepin-1-yl]ethanoic acid amide was added, and the reaction refluxed for an additional 18 hours. The reaction mixture was then chromatographed on silica gel using ethyl acetate in methylene chloride as eluant to afford the product as an oil, 410 mg (93%), which was triturated to a solid with isopropyl ether, 290 mg (66%), M.P. 150°–160° C.

$^1$H NMR (δ, CDCl$_3$): 1.25 (s, 9H), 2.31 (s, 3H), 2.7–3.0 (m, 3H), 3.27 (AB$_q$, J$_{AB}$=16, Δv=274), 3.77 (s, 3H), 4.15 (m, 1H), 4.61 (m, 1H), 6.08 (s, 1H), 6.59 (d, 1H), 6.9–7.5 (m, 11H), 7.96 (s, 1H), 8.08 (s, 1H).

$^{13}$C. NMR (δ, DMSO-d$_6$): 21.1, 28.6, 37.2, 43.9, 50.2, 51.6, 52.0, 60.4, 119.9, 123.2, 123.3, 123.5, 126.2, 126.3, 128.3, 128.5, 128.7, 130.4, 130.6, 135.1, 139.0, 139.8, 141.0, 142.0, 155.1, 167.2, 167.4, 171.2, 173.

IR (KBr, cm.$^{-1}$): 1682, 1668, 1652 (C=O)

MS (%): 557 (70, parent+1), 484 (100), 307 (37), 234 (48), 208 (7), 119 (5).

Anal. Calc'd for C$_{32}$H$_{36}$N$_4$O$_5$: C, 69.05; H, 6.52;N, 10.06. Found: C, 68.84; H, 6.59;N, 9.99.

EXAMPLE 34

N-(1-t-butyl)-2-[3-((3-carboxy)phenyl)ureido)-2-oxo-5-phenyl)-8-methyl-2,3,4,5-tetrahydro-1H-(1)benzazepin-1yl]ethanoic acid amide To a 100 ml round-bottomed flask equipped with a nitrogen inlet were added 75 mg (0.135 mmol) N-(1-t-butyl)-2-[3-((3-carbomethoxy)phenyl)ureido)-2-oxo-5-(phenyl)-8-methyl-2,3,4,5-tetrahydro-1H-(1)benzazepin-1yl]ethanoic acid amide, 3 mL tetrahydrofuran and a solution of 28 mg (0. 674 mmol) lithium hydroxide hydrate in 1 mL water. Methanol (3 mL ) was added to give a solution, and the reaction stirred at room temperature for 18 hours. It was then poured into 0.5N hydrochloric acid, extracted into ethyl acetate, and the organic layer was washed with brine and dried over sodium sulfate. After evaporation, the residue was slurried in ethyl acetate and filtered to afford a white solid, M.P. 266°–267° C., 42 mg (57%).

$^1$H NMR (δ, DMSO-d$_6$): 1.23 (s, 9H), 2.31 (s, 3H), 2.58 (m, 1H), 2.9 (m, 2H), 3.31 (m, 1H), 3.33 (AB$_q$, J$_{AB}$=16, Δv=267), 4.32 (m, 2H), 4.46 (m, 1H), 6.69 (m, 1H), 7.0–7.6 (m, 12H), 8.00 (s, 1H), 9.06 (s, 1H).

$^{13}$C NMR (δ, DMSO-d$_6$): 20.8, 28.5, 43.1, 48.9, 50.3, 52.0, 118.3, 121.6, 122.0, 122.2, 124.8, 1215–9, 126.4, 127.5, 127.6, 128.0, 128.1, 128.8, 128.9, 130.6, 131.4, 134.8, 137.9, 140.5, 141.6, 142.7, 154.0, 167.0, 167.3, 170.3.

Anal. Calc'd for C$_{31}$H$_{34}$N$_4$O$_5$.H$_2$: C., 66.41; H, 6.47; N, 9.99. Found: C, 66.60; H, 6.20; N, 9.81.

EXAMPLE 35

N-(1-t-butyl)-2-[3-((3-N-(methanesulfonamido)carboxamido)phenyl)ureido)-2-oxo-5-(phenyl)-8-methyl-2,3,4,5-tetrahydro-1H-(1)benzazepin-1-yl]ethanoic acid amide Prepared in 20% yield as a foam by condensing methanesulfonamide with N-(1-t-butyl)-2-[3-((3-carboxy)phenyl)ureido)-2-oxo-5-(phenyl)-8-methyl-2,3,4,5-tetrahydro-1H-(1)benzazepin-1-yl]ethanoic acid amide in the presence of ethyl(dimethylamino-propyl)carbodiimide and 4-dimethylaminopyridine in dimethylformamide.

$^1$H NMR (δ, CDCl$_3$): 1.10 (s, 9H), 1.9 (m, 1H), 2.40 (s, 3H), 2.87 (m, 2H), 3.28 (AB$_q$, J$_{AB}$=16, Δv=133), 3.34 (s, 3H), 4.24 (m, 1H), 4.46 (m, 1H), 4.78 (m, 1H), 5.23 (m, 1H), 6.8–7.5 (m, 12H), 7.73 (m, 1H).

FAB Mass Spectroscopy (%): 620 (parent+1, 45), 547 (83), 307 (53), 234 (95), 208 (100).

EXAMPLE 36

N-(1-t-butyl)-2-[3-((3-N-(phenylsulfonamido)carboxamido)phenyl)ureido)-2-oxo-5-(phenyl)-8-methyl-2,3,4,5-tetrahydro-1H-(1)-benzazepin-1-yl]ethanoic acid amide Prepared in 53% yield, M.P.=180°–190° C. by condensing phenylsulfonamide with N-(1-t-butyl)-2-[3-((3-carboxy)phenyl)ureido)-2-oxo-5-(phenyl)-8-methyl-2,3,4,5-tetrahydro-1H-(1)benzazepin-1-yl]ethanoic acid amide in the presence of ethyl(dimethylaminopropyl)carbodiimide and 4-dimethylaminopyridine in dimethylformamide.

$^1$H NMR (δ, CDCl$_3$): 1.09 (s, 9H), 2.34 (s, 3H), 2.4 (m, 1H), 2.95 (m, 2H), 3.31 (AB$_q$, J$_{AB}$=16, Δv=124), 4.27 (m, 1H), 4.82 (m, 1H), 5.42 (m, 1H), 6.69 (m, 1H), 7.0–7.5 (m, 15H), 7.73 (m, 1H), 8.05 (m, 2H).

$^{13}$C NMR (δ, CDCl$_3$): 21.0, 28.6, 28.7, 37.3, 43.9, 49.7, 51.9, 53.4, 118.7, 122.4, 123.6, 125.7, 126.2, 126.6, 128.3, 128.4, 128.7, 130.5, 131.4, 133.2, 135.1, 138.7, 139.6, 139.9, 140.8, 142.1, 155.6, 165.4, 166.8, 174.7.

I claim:

1. A compound of the formula

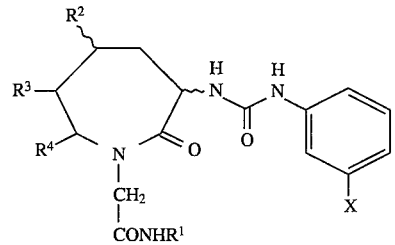 I wherein R$^1$ is (C$_1$–C$_{10}$)alkyl;

R$^2$ is phenyl or (C$_1$–C$_{10}$)alkyl, each of which may be substituted by Y$^1$;

R$^3$ and R$^4$ are independently selected from the group consisting of hydrogen, (C$_1$–C$_{10}$)alkyl and phenyl, or may be taken together with the two carbons to which they are attached to form a phenyl which may be substituted by Y$^2$;

X is tetrazolyl or

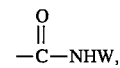

wherein W is selected from

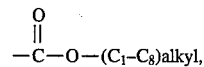

—SO$_2$(C$_1$–C$_8$)alkyl,    —SO$_2$NH(C$_1$–C$_8$)alkyl,
—SO$_2$CF$_3$,

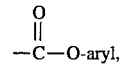

—SO$_2$(phenyl),   —SO$_2$(benzyl),   —SO$_2$NH(phenyl),
—SO$_2$NH(heteroaryl) and —SO$_2$(heteroaryl), wherein said heteroaryl is a 5 to 7 membered saturated or unsaturated hydrocarbon ring containing one to four heteroatoms selected from oxygen, nitrogen and sulfur and wherein the phenyl and heteroaryl moieties of W may optionally be substituted with one or two substituents independently selected from $(C_1-C_6)$alkyl optionally substituted with from one to three fluorine atoms, phenyl, halo, $(C_1-C_6)$alkoxy optionally substituted with from one to three fluorine atoms,

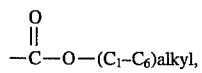

—$SO_2$, —$SO_2NH(C_1-C_6)$alkyl,

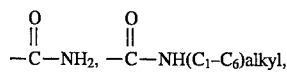

cyano and —$S(C_1-C_6)$alkyl; and $Y^1$ and $Y^2$ are independently selected from the group consisting of hydrogen, thienyl, pyridyl, furyl, and pyrimidyl, halo, $(C_1-C_6)$ alkyl optionally substituted with from one to three fluorine atoms, $(C_1-C_6)$ alkoxy optionally substituted with from one to three fluorine atoms, nitro, cyano, amino, —$NH(C_1-C_6)$alkyl, —$N[(C_1-C_8)$alkyl$]_2$, —$S$—$(C_1-C_8)$alkyl, —$SO$—$(C_1-C_8)$alkyl, —$SO_2$—$(C_1-C_8)$alkyl,

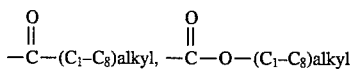

and phenyl, wherein said phenyl may optionally be substituted with one or two substituents independently selected from halo, $(C_1-C_6)$alkyl, $(C_1-C_6)$alkoxy, nitro, cyano, amino and trifluoromethyl;

or a pharmaceutically acceptable salt thereof.

2. A compound according to claim 1, wherein $R^2$ is phenyl, isopropyl or cyclohexyl.

3. A compound according to claim 1, wherein $R^3$ is hydrogen and $R^4$ is phenyl.

4. A compound according to claim 1, wherein $R^3$ and $R^4$ are taken together with the two carbons to which they are attached to form a phenyl group.

5. A compound according to claim 1, wherein $R^2$ is phenyl, $R^3$ is hydrogen and $R^4$ is phenyl.

6. A compound according to claim 1, wherein $R^2$ is phenyl and $R^3$ and $R^4$ are taken together with the two carbons to which they are attached to form a phenyl group.

7. A compound according to claim 1, wherein $R^2$ is isopropyl and $R^3$ and $R^4$ are taken together with the two carbons to which they are attached to form a phenyl group.

8. A compound according to claim 1, wherein $R^2$ is cyclohexyl and $R^3$ and $R^4$ are taken together with the two carbons to which they are attached to form a phenyl group.

9. A compound according to claim 1, wherein x is $CONHSO_2(C_1-C_8)$alkyl or tetrazolyl.

10. A compound according to claim 1 that is selected from:

N-(1-t-butyl)-2-[3-((3-N-(methanesulfonamido)carboxamido)phenyl)ureido)-2-oxo-5-(phenyl)-8-methyl-2,3,4,5-tetrahydro-1H-(1)benzazepin-1-yl] ethanoic acid amide; and N-(1-t-butyl)-2-[3-((3-N-(phenylsulfonamido)carboxamido)phenyl)ureido)-2-oxo-5-(phenyl)-8-methyl-2,3,4,5-tetrahydro-1H-(1)benzazepin-1-yl] ethanoic acid amide.

11. A pharmaceutical composition for (a) treating or preventing a condition selected from the group consisting of pain, gastrointestinal disorders such as ulcer and colitis, and central nervous system disorders such as anxiety and panic disorder in a mammal or (b) antagonizing the effects of cholecystokinin in a mammal, comprising an amount of a compound according to claim 1 effective in preventing or treating such condition and a pharmaceutically acceptable carrier.

12. A method of treating or preventing a condition selected from the group consisting of pain, gastrointestinal disorders such as ulcer and colitis, and central nervous system disorders such as anxiety and panic disorder in a mammal, comprising administering to a mammal in need of such treatment or prevention an amount of a compound according to claim 1 effective in treating or preventing such condition.

13. A method of antagonizing the effects of cholecystokinin in a mammal, comprising administering to said mammal a cholecystokinin-B antagonizing effective amount of a compound according to claim 1.

* * * * *